(12) United States Patent
Albrecht et al.

(10) Patent No.: US 10,254,281 B2
(45) Date of Patent: Apr. 9, 2019

(54) AUTOANTIGEN IN IDIOPATHIC INFLAMMATORY MYOPATHIES

(71) Applicant: Stiftelsen Vectis, Stockholm (SE)

(72) Inventors: Inka Albrecht, Solna (SE); Ingrid Lundberg, Stockholm (SE); Cecilia Wick, Hässelby (SE); Åsa Hallgren, Uppsala (SE); Olle Kämpe, Uppsala (SE)

(73) Assignee: STIFTELSEN VECTIS, Stockholm (SE)

( * ) Notice: Subject to any disclaimer, the term of this patent is extended or adjusted under 35 U.S.C. 154(b) by 0 days.

(21) Appl. No.: 15/526,851

(22) PCT Filed: Nov. 10, 2015

(86) PCT No.: PCT/SE2015/051189
§ 371 (c)(1),
(2) Date: May 15, 2017

(87) PCT Pub. No.: WO2016/080887
PCT Pub. Date: May 26, 2016

(65) Prior Publication Data
US 2017/0328899 A1    Nov. 16, 2017

(30) Foreign Application Priority Data
Nov. 17, 2014 (SE) ...................................... 1430161

(51) Int. Cl.
*G01N 33/50* (2006.01)
*G01N 33/564* (2006.01)
*A61K 39/00* (2006.01)
*A61K 38/17* (2006.01)
*G01N 33/68* (2006.01)

(52) U.S. Cl.
CPC .......... *G01N 33/564* (2013.01); *A61K 38/17* (2013.01); *A61K 38/1709* (2013.01); *A61K 39/00* (2013.01); *G01N 33/6887* (2013.01)

(58) Field of Classification Search
None
See application file for complete search history.

(56) References Cited

U.S. PATENT DOCUMENTS

| 9,664,687 B2 * | 5/2017 | Nagele ............... G01N 33/6854 |
| 2014/0162259 A1 * | 6/2014 | Vincent .................. C07K 14/47 435/6.11 |
| 2014/0315736 A1 | 10/2014 | Nagele |

FOREIGN PATENT DOCUMENTS

WO    2008107201    3/2008

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013) (Year: 2013).*
Torzewski et al., Animal Models of C-Reactive Protein, Hindawl Publishing Corporation, Mediators of Inflammation, vol. 2014, Article ID 683598, 2014, pp. 1-7.    W  (Year: 2014).*
International Search Report issued in parent international application No. PCT/SE2015/051189, dated Feb. 18, 2016, pp. 1-2.
D'Arcy, "Identification of FHL1 as a therapeutic target for Duchenne muscular dystrophy," Human Molecular Genetics, 2014 (Puglished online Sep. 18, 2013), vol. 23, No. 3, pp. 618-636.
Written Opinion issued in parent international application No. PCT/SE2015/051189, dated Feb. 18, 2016, pp. 1-11.
Cowling, "Identification of FHL1 as a regulator of skeletal muscle mass: implications for human myopathy," published Dec. 15, 2008, jcb.rupresss.org, pages J. Cell Biology VO. 183, No. 6 pp. 1033-1048.
Albrecht, "Development of autoantibodies against muscle-specific FHL1 in severe inflammatory myopathies," The Journal of Clinical Investigation, jci.org, vol. 125, No. 12, Dec. 2015, pp. 4612-4624.
Domenighetti, "Loss of FHL1 induces an age-dependent skeletal muscle myopathy associated with myofibrillar and intermyofibrillar disorganization in mice," Human Molecular Genetics, 2014, vol. 23, No. 1, pp. 209-225.
Salajegheh, "Autoantibodies against a 43 KDa muscle protein in inclusion body myositis," www.plosone.org, May 2011, vol. 6, Issue 5, pp. 1-3.

* cited by examiner

*Primary Examiner* — Gary Counts
(74) *Attorney, Agent, or Firm* — Jeffrey S. Melcher; Melcher Patent Law PLLC

(57) ABSTRACT

FHL1 (Four-and-a-half-LIM domain 1) is identified as a new muscle specific autoantigen. Detection of autoantibodies for FHL1 in a sample obtained from a human subject are useful for diagnosis of autoimmune muscle diseases, including myositis, polymyositis, dermatomyositis, inclusion body myositis, and immune mediated necrotizing myopathy. FHL1 and FHL1 derived peptides are used for the treatment of autoimmune muscle diseases.

9 Claims, 16 Drawing Sheets

Figure 1:
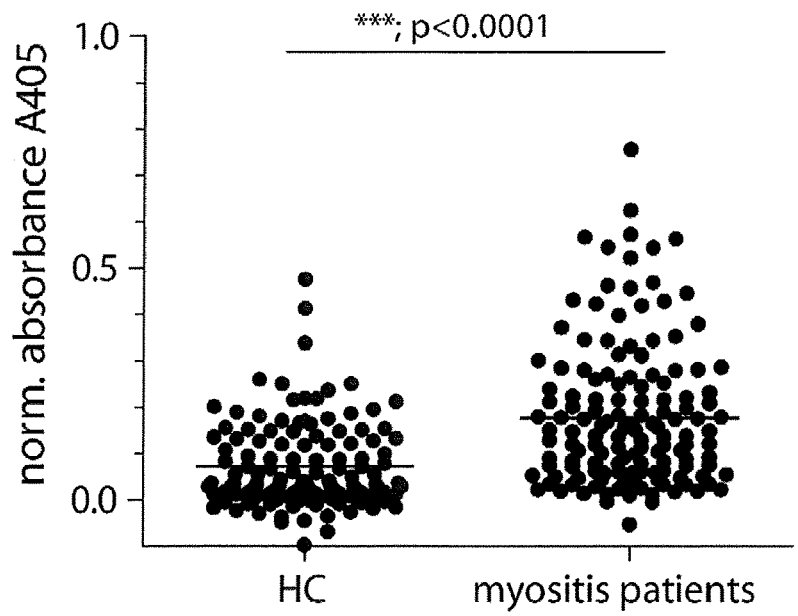
Figure 1:
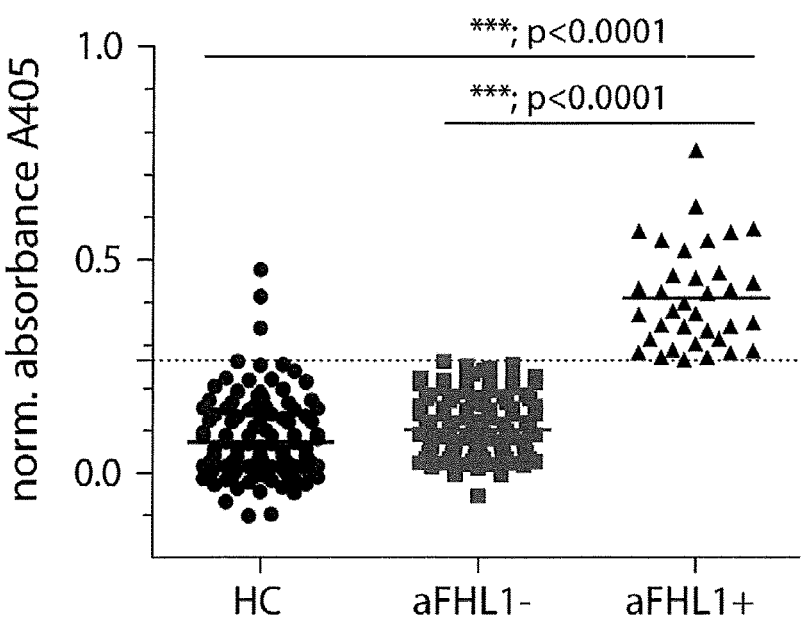
Figure 1:
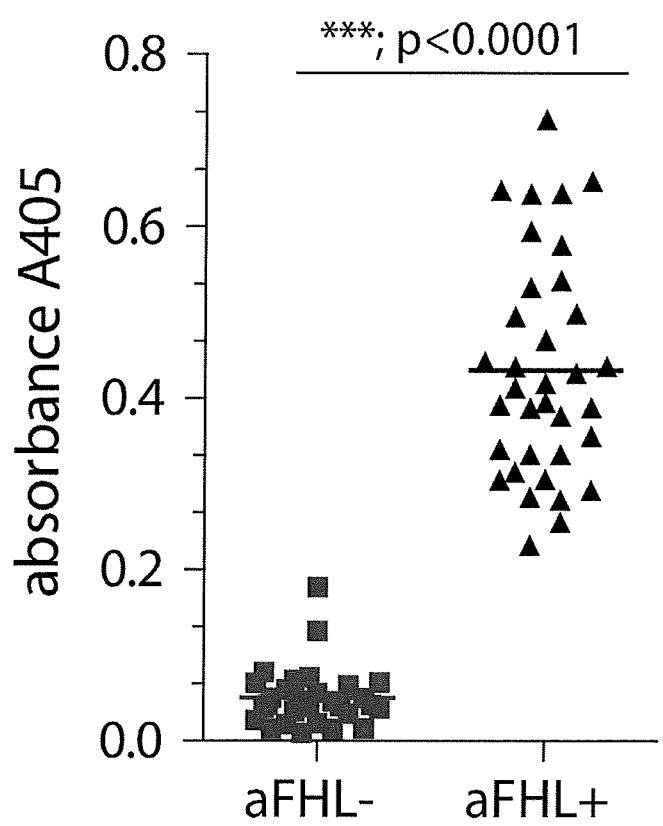
Figure 1:
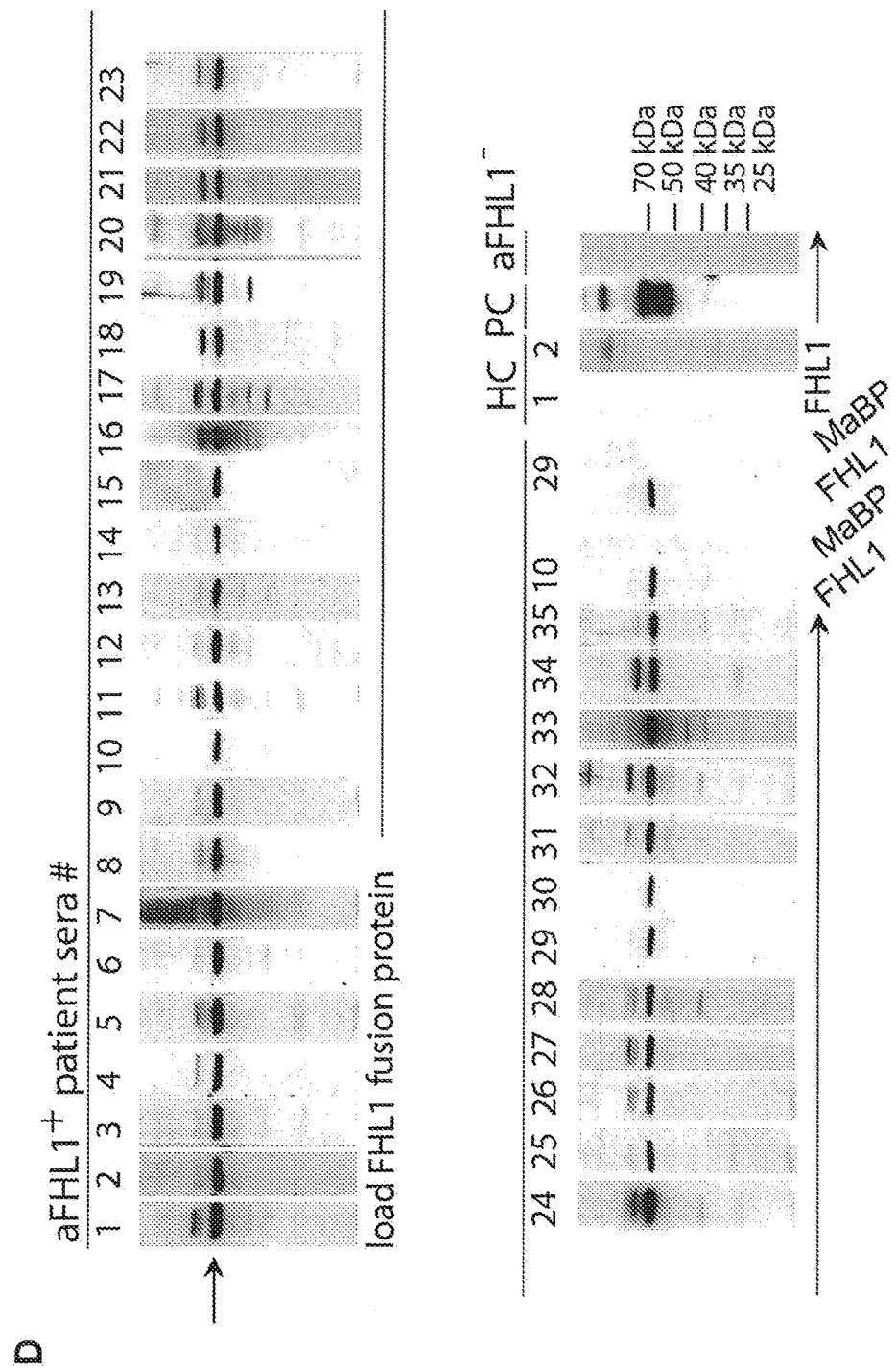

Specification includes a Sequence Listing.

B

C

A

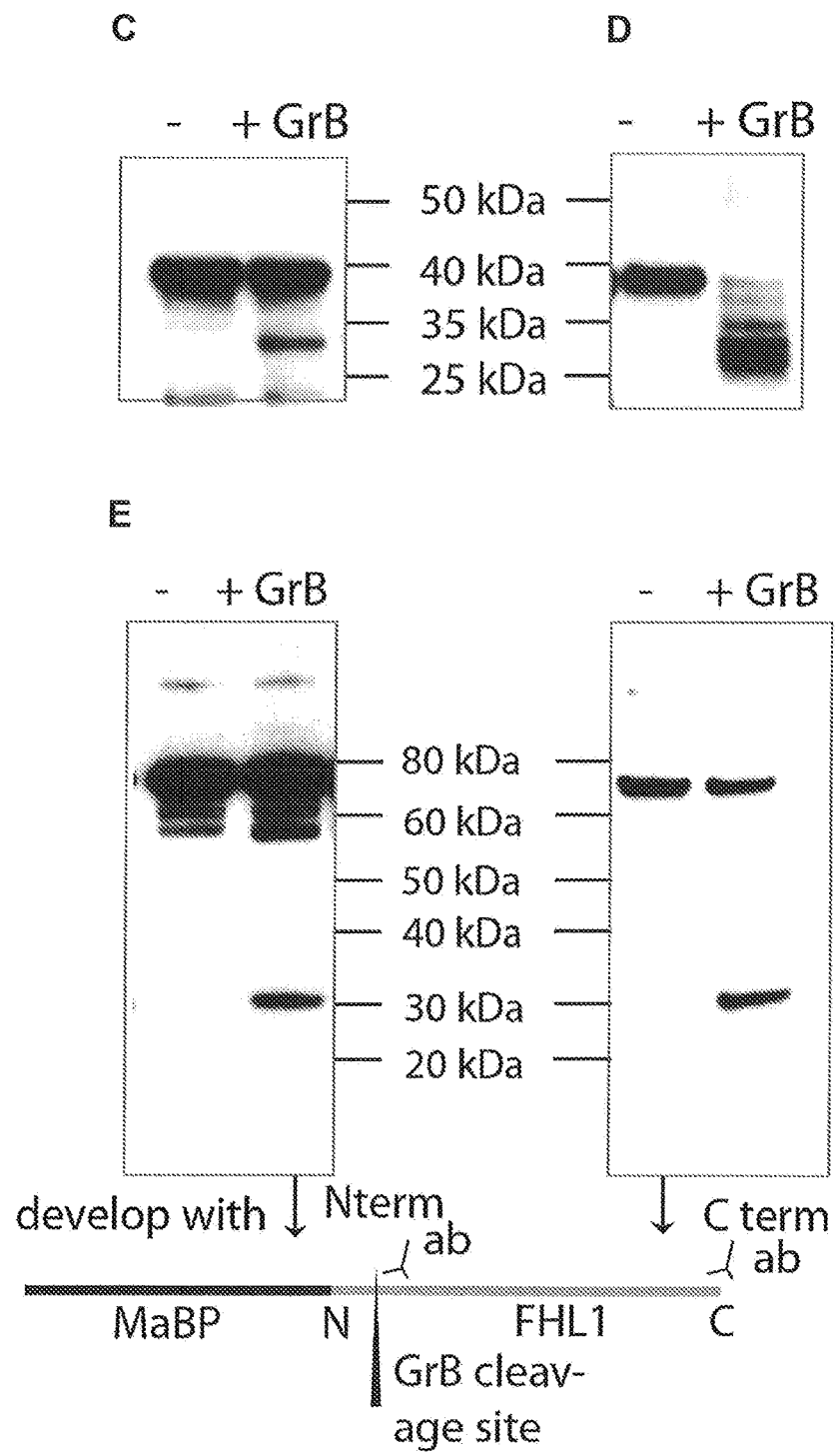

F

G

AUTOANTIGEN IN IDIOPATHIC INFLAMMATORY MYOPATHIES

FIELD OF THE INVENTION

The present invention relates to the fields of medicine, diagnostics and muscle disease. More particular, FHL1 (Four-and-a-half-LIM domain 1) has been identified as a new muscle specific autoantigen in idiopathic inflammatory myopathies (IIM). The invention specifically relates to methods detecting anti-FHL1 autoantibodies, which represent peripheral blood biomarkers for diagnosis of a new subset of IIM characterized by pronounced skeletal muscle involvement and poor prognosis, as well as the use of FHL1 and FHL1 derived peptides for the treatment of muscle diseases.

BACKGROUND OF THE INVENTION

Idiopathic inflammatory myopathies (IIMs), collectively called myositis, are a group of rare, systemic autoimmune diseases. The skeletal muscle is attacked by cells of the immune system consequently leading to proximal muscle weakness and in many individuals extra-muscular manifestations including fever, interstitial lung disease, and arthritis or skin rash. Several forms of the disease can be distinguished based on clinical features, autoantibody profiles and muscle histopathology. The commonly used nomenclature includes polymyositis, dermatomyositis, inclusion body myositis (IBM) and immune mediated necrotizing myopathy (Dalakas et al. *The immunopathologic and inflammatory differences between dermatomyositis, polymyositis and sporadic inclusion body myositis*. Curr Opin Neurol 1996, 9(3):235-239; Greenberg. *Proposed immunologic models of the inflammatory myopathies and potential therapeutic implications*. Neurology 2007, 69(21):2008-2019; Ernste et al. Idiopathic inflammatory myopathies: current trends in pathogenesis, clinical features, and up-to-date treatment recommendations. Mayo Clin Proc 2013, 88(1):83-105; Emslie-Smith et al. *Necrotizing myopathy with pipestem capillaries, microvascular deposition of the complement membrane attack complex (MAC), and minimal cellular infiltration*. Neurology 1991, 41(6):936-939; Bronner et al. *Necrotising myopathy, an unusual presentation of a steroid-responsive myopathy*. J Neurol 2003, 250(4):480-485; Liang et al. *Necrotizing autoimmune myopathy*. Curr Opin Rheumatol 2011, 23(6):612-619; Grable-Esposito et al. *Immune-mediated necrotizing myopathy associated with statins*. Muscle Nerve 2010, 41(2):185-190; Christopher-Stine et al. *A novel autoantibody recognizing 200-kd and 100-kd proteins is associated with an immune-mediated necrotizing myopathy*. Arthritis Rheum 2010, 62(9):2757-2766; Griggs et al. *Inclusion body myositis and myopathies*. Ann Neurol 1995, 38(5):705-713).

More recently a number of studies suggest that the autoantibody status of myositis patients defines more specific disease clinical phenotypes including extramuscular organ involvement and treatment response. Myositis-specific autoantibodies can be detected in the serum of approximately 50-60% of myositis patients. The most frequent specificities are autoantibodies against aminoacyl transfer RNA (tRNA) synthetases including histidyl-tRNA synthetase (Jo-1) (Mathews et al. *Myositis autoantibody inhibits histidyl-tRNA synthetase: a model for autoimmunity*. Nature 1983, 304(5922):177-179); approximately 20-25% of patients with IIM show this reactivity (Gunawardena et al. *Myositis-specific autoantibodies: their clinical and pathogenic significance in disease expression*. Rheumatology (Oxford) 2009, 48(6):607-612; Targoff: *Myositis specific autoantibodies*. Curr Rheumatol Rep 2006, 8(3):196-203). Other frequently detected autoantibodies are anti-TIF1 gamma (p155/140), anti-Mi-2, anti-SRP, and anti-MDA-5 (CADM-140) antibodies (Betteridge et al. *Novel autoantibodies and clinical phenotypes in adult and juvenile myositis*. Arthritis Res Ther 2011, 13(2):209; Gunawardena et al. *Clinical associations of autoantibodies to a p155/140 kDa doublet protein in juvenile dermatomyositis*. Rheumatology (Oxford) 2008, 47(3):324-328; Targoff et al. *The association between Mi-2 antibodies and dermatomyositis*. Arthritis Rheum 1985, 28(7):796-803; Targoff et al. *Antibody to signal recognition particle in polymyositis*. Arthritis Rheum 1990, 33(9):1361-1370; Gono et al. *Clinical manifestation and prognostic factor in anti-melanoma differentiation-associated gene 5 antibody-associated interstitial lung disease as a complication of dermatomyositis*. Rheumatology (Oxford) 2010, 49(9):1713-1719). All these autoantibodies are, however, directed against ubiquitously expressed proteins of the cytoplasm or the cell nucleus. Until now, little is known about autoantigens predominantly expressed in the skeletal muscle although a few targets have recently been described as biomarkers for the IIM subtype IBM (Salajegheh et al. *Autoantibodies against a 43 KDa muscle protein in inclusion body myositis*. PLoS One 2011, 6(5):e20266; Larman et al. *Cytosolic 5'-nucleotidase 1A autoimmunity in sporadic inclusion body myositis*. Ann Neurol 2013, 73(3):408-418). Identifying and characterizing novel muscle-specific autoantigens involved in immune-mediated processes during muscle dysfunctions could help to explain how a chronic autoimmune attack of the skeletal muscle initiates and progresses.

Four-and-a-half-LIM domain 1 (FHL1) is a member of the FHL family of proteins characterized by four and a half highly conserved LIM domains. LIM domains are cysteine-rich, tandem zinc finger motifs mediating protein-protein interactions. Several spliced variants of FHL1 have been identified containing additional domains resulting in differential intracellular localization, protein interactions and functions (Shathasivam et al. *Genes, proteins and complexes: the multifaceted nature of FHL family proteins in diverse tissues*. J Cell Mol Med 2010, 14(12):2702-2720). The major isoforms are FHL1 isoform A (containing 4 and ½ LIM domain, predicted molecular size 32 kDa), isoform B (containing 3 and ½ LIM domain, a nuclear localization and export sequences and a binding site for RBP-J (recombination signal binding protein for immunoglobulin kappa J region) region, predicted molecular size 36 kDa) and the short isoform C (containing 2 and ½ LIM domain A and a RBP-J region, predicted molecular size 22 kDa). A variety of interactions with different proteins have been described, either with components of the cytoskeleton to scaffold cytoskeletal and signalling complexes or in the nucleus to regulate gene transcription. Since FHL1 is predominantly expressed in the skeletal muscle, all of these protein interactions translate into a multifunctional role of FHL1 in muscle growth and differentiation, structural maintenance including assembly of the sarcomere as well as cell signalling, although the precise molecular mechanisms are largely unknown (Shathasivam ibid; McGrath et al. *Four and a half LIM protein 1 binds myosin-binding protein C and regulates myosin filament formation and sarcomere assembly*. J Biol Chem 2006, 281(11):7666-7683; Cowling et al. *Four and a half LIM protein 1 gene mutations cause four distinct human myopathies: a comprehensive review of the clinical, histological and pathological features*. Neuromuscul Disord 2011, 21(4):237-251). Most importantly, several genetic FHL1 mutations have been identified that are causative for numerous different X-linked myopathies such as reducing body myopathy (RBM) (Schessl et al. *Familial reducing body myopathy with cytoplasmic bodies and rigid spine revisited: identification of a second LIM domain mutation in FHL1*. Neuropediatrics 2010, 41(1):43-46; Schessl et al. *Clinical, histological and genetic characterization of reducing body myopathy caused by mutations in FHL1*. Brain 2009, 132(Pt 2):452-464; Schessl et al. *Proteomic identification of FHL1 as the protein mutated in human reducing body myopathy*. J Clin Invest 2008, 118(3):904-912; Shalaby et al. *Novel FHL1 mutations in fatal and benign reducing body myopathy*. Neurology 2009, 72(4):375-376), X-linked myopathy characterized by postural muscle atrophy (XMPMA) (Schoser et al. *Consequences of mutations within the C terminus of the FHL1 gene*. Neurology 2009, 73(7):543-551; Windpassinger et al. *An X-linked myopathy with postural muscle atrophy and generalized hypertrophy, termed XMPMA, is caused by mutations in FHL1*. Am J Hum Genet 2008, 82(1):88-99), scapuloperoneal myopathy (SPM) (Chen et al. *A novel mutation in FHL1 in a family with X-linked scapuloperoneal myopathy: phenotypic spectrum and structural study of FHL1 mutations*. J Neurol Sci 2010, 296(1-2):22-29) and Emery-Dreifuss muscular dystrophy (EDMD) (Gueneau et al. *Mutations of the FHL1 gene cause Emery-Dreifuss muscular dystrophy*. Am J Hum Genet 2009, 85(3):338-35). These diseases are rare hereditary muscle disorders that mainly affect children or individuals of young age. Although FHL1-associated myopathies share some overlapping pathological features, they differ in respect to severity of muscle weakness ranging from development of scoliosis, spinal rigidity, progressive muscle loss till complete loss of ambulation and death caused by respiratory or heart failure (Cowling ibid). A molecular explanation might be protein instability because of a possible destruction of the zinc finger motif consequently leading to protein aggregation and degradation (Schessl ibid). All these studies indicate that FHL1 is critical for a healthy skeletal muscle structure and functionality.

SUMMARY OF THE INVENTION

The present inventors have identified Four and a half LIM domain 1 (FHL1) as a novel major muscle-specific autoantigen associated with myositis. FHL1 autoantibodies are significantly associated with distal muscle weakness, clinical atrophy, dysphagia as well as a poor clinical outcome and fiber necrosis and connective tissue/fat replacement as evident by clinical and muscle biopsy features.

A first aspect of the present invention provides methods for the diagnosis of autoimmune muscle diseases. The methods comprise detection of autoantibodies specific for FHL1 in a sample obtained from a subject. In one embodiment, the methods can be used for assessing the subject's risk of developing an autoimmune muscle disease. In another embodiment, the methods can be used for assessing the severity and/or the prognosis of the autoimmune muscle disease. In another embodiment, the methods can be used for determining whether the subject is likely to benefit from a specific form of treatment or not, the specific form of treatment can be treatment with FHL1 and/or peptide fragments derived from FHL1.

The subject can be a human. The sample can be a blood sample, such as serum or plasma.

The autoimmune muscle disease can be an idiopathic inflammatory myopathy.

Antibodies specific for FHL1 can be detected using an immunoassay, such as ELISA, RIA, or radioimmunoprecipitation assays, by surface plasmon resonance, or by electrochemiluminescence.

A second aspect of the present invention provides FHL1 and/or a peptide fragment derived from FHL1 for use in the treatment of autoimmune muscle diseases.

Accordingly, the second aspect of the present invention provides a pharmaceutical composition comprising therapeutically effective amount of FHL1 and/or a peptide fragment derived from FHL1 for use in the treatment of autoimmune muscle diseases.

Put another way, the second aspect of the present invention provides for use of FHL1 and/or a peptide fragment derived from FHL1 in the manufacture of a pharmaceutical composition for use in the treatment of autoimmune muscle diseases.

In one embodiment, the invention provides a method for the treatment of an autoimmune muscle disease which comprises administering a therapeutically active amount of FHL1 and/or a peptide fragment derived from FHL1 to a patient in need of such treatment.

The autoimmune muscle disease can be an idiopathic inflammatory myopathy.

Preferably, the autoimmune muscle disease is characterized by the presence of autoantibodies specific to FHL1.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These and other embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the original description, and the invention includes all such substitutions, modifications, additions and/or rearrangements.

LEGENDS TO FIGURES

FIG. 1: Patients with inflammatory myopathies show reactivity to FHL1.

(A) Sera of 141 patients with myositis (polymyositis, dermatomyositis or inclusion body myositis) were analyzed by ELISA for reactivity to recombinant FHL1-MaBP fusion protein and compared to gender and age-matched healthy controls (HC, n=126).

(B) According to the normalized absorbance values of the HCs, a cut-off value was calculated allowing subdivision of the patients into anti-FHL1-negative (aFHL1−) and anti-FHL1-positive (aFHL1+) patients. The cut-off value was defined as mean [norm Absorbance HC]+2*SD=0.26228. Autoantibody positivity was confirmed by another ELISA using a recombinant His-tagged FHL1 comparing the 35 anti-FHL1+ patients to 30 gender- and age-matched anti-FHL1− patients (C) and by western blot using recombinant FHL1-MaBP fusion protein (D). All 35 anti-FHL1$^+$ patients were analyzed by western blot. As controls 2 HC sera ($3^{rd}$ and 4$^{th}$ lane from back) and 1 anti-FHL1− serum (last lane) was used; moreover, for anti-FHL1+ patients 10 and 29, recombinant MaBP only was loaded next to FHL1-MaBP (4 lanes after serum 35). For positive control (PC), western blot was developed with a commercially available antibody (2$^{nd}$ lane from back). Statistical analysis for A, B and C: two-tailed Mann Whitney test; each data point represents one individual and horizontal bars indicate mean values.

Figure 2:
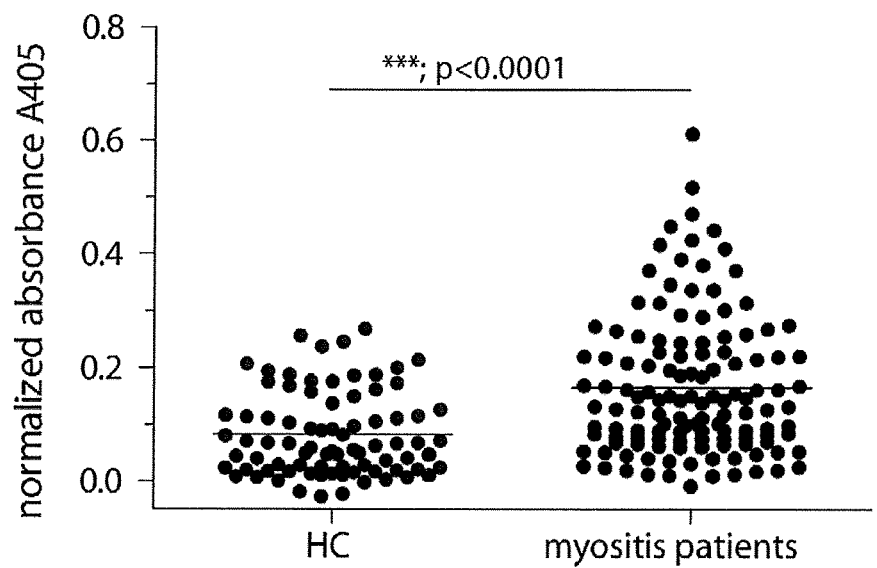
Figure 2:
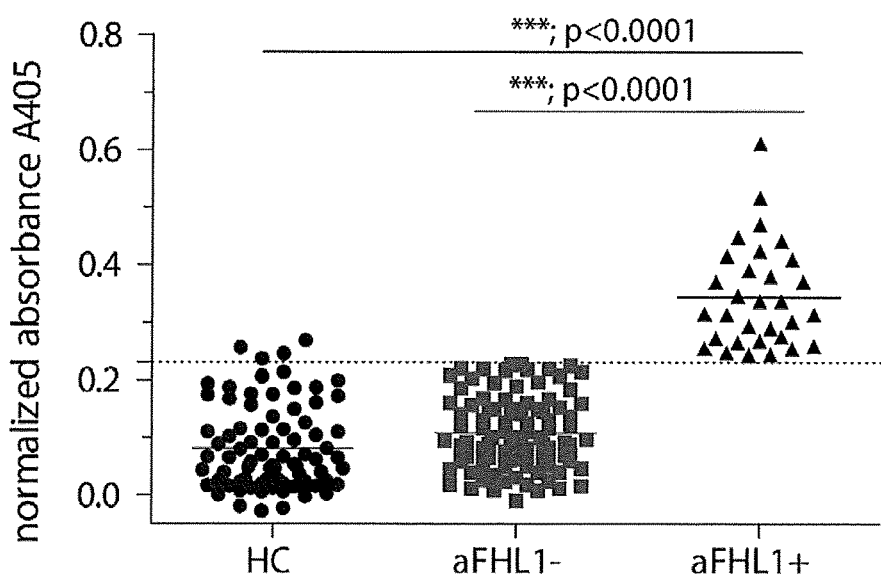

FIG. 2: Patients with inflammatory myopathies show reactivity to FHL1—examination of a cohort from the Czech Republic.

(A) Sera of 129 IIM patients from a Czech cohort were analyzed by ELISA for reactivity to recombinant FHL1-MaBP fusion protein and compared to 81 healthy controls from Czech Republic (HC). (B) According to the normalized absorbance values of the HCs, a cut-off value (line) was calculated allowing subdivision of the patients into anti-FHL1-negative (a-FHL1$^-$) and anti-FHL1-positive (a-FHL1$^+$) patients. Statistical analysis: two-tailed Mann Whitney test. Each data point represents one individual and horizontal bars indicate mean values.

Figure 3:
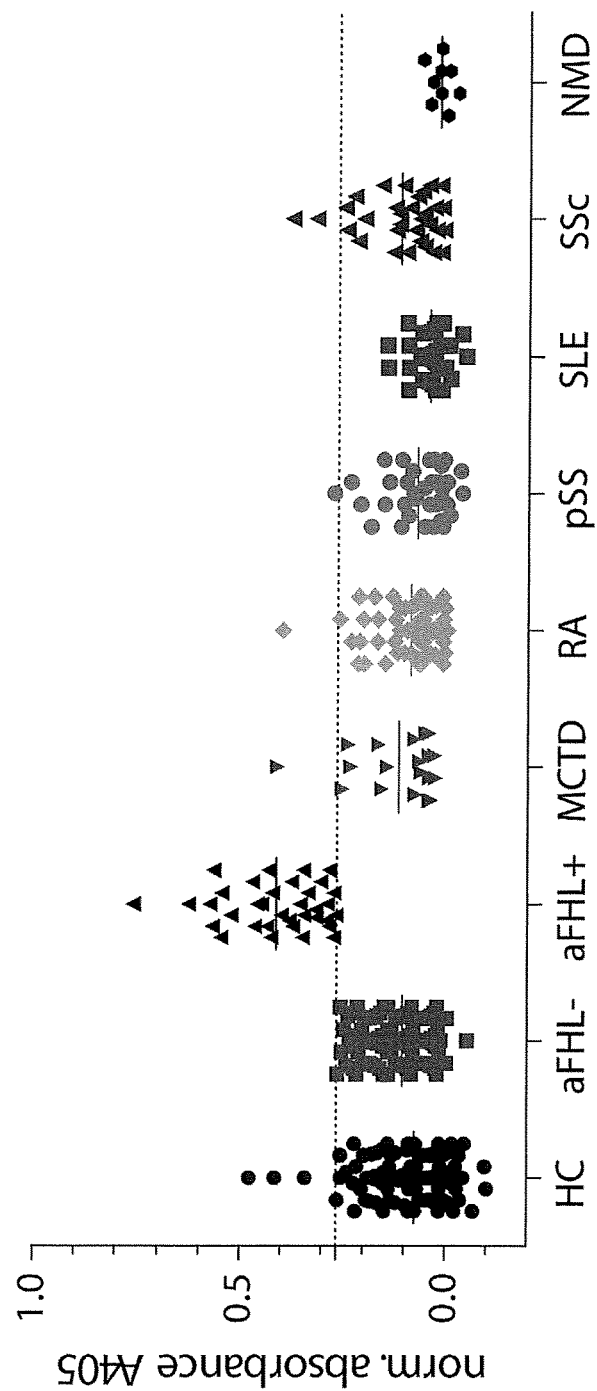

FIG. 3: Anti-FHL1 autoantibodies are myositis specific.

Reactivity to FHL1 in sera from myositis patients (n=141) was compared by FHL1-MaBP ELISA to reactivity measured in sera from patients with other autoimmune diseases such as mixed-connective tissue disease (MCTD, n=19), rheumatoid arthritis (RA, n=67), Sjögren's syndrome (pSS, n=35), systemic lupus erythematosus (SLE, n=33), and systemic sclerosis (Ssc, n=32), as well as to sera from patients with genetically based neuromuscular diseases (NMD, n=9). When possible (for RA, pSS, SLE and Ssc), those patients were gender and age-matched to myositis patients showing positivity for anti-FHL1 antibodies. Each data point represents one individual and horizontal bars indicate mean values. The line represents the cut-off value described in FIG. 1.

Figure 4:
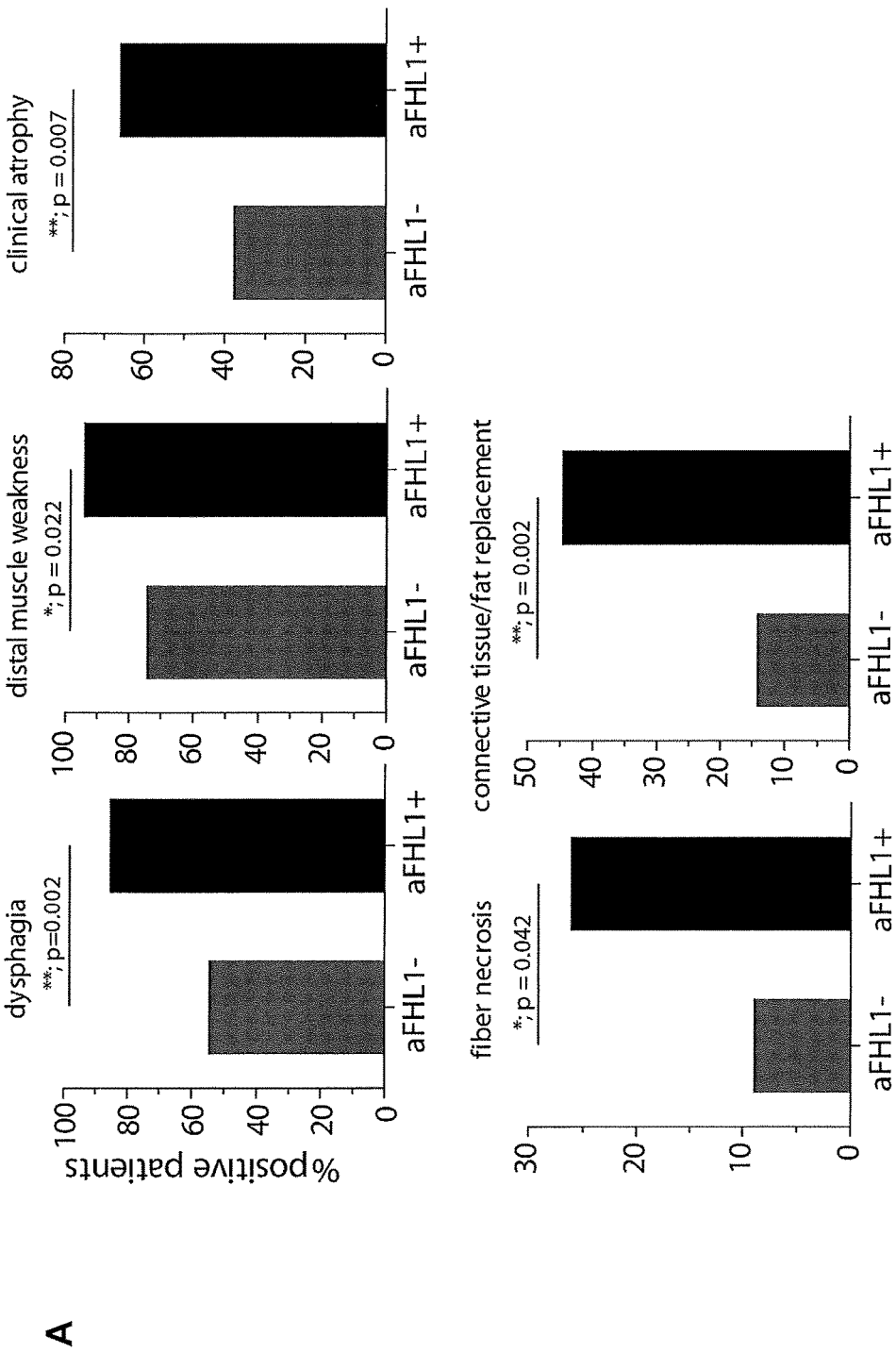
Figure 4:
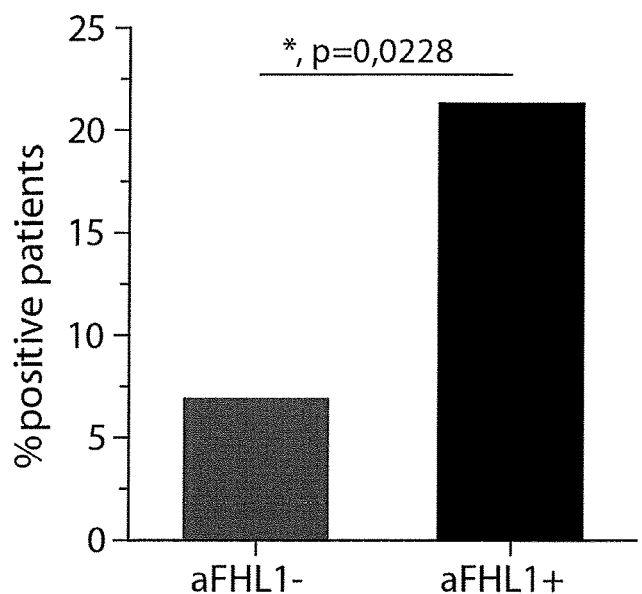
Figure 4:
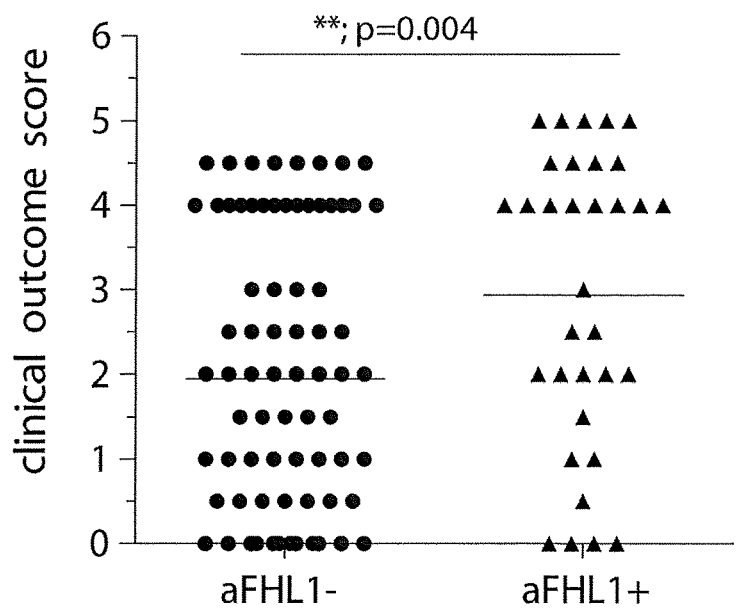
Figure 4:
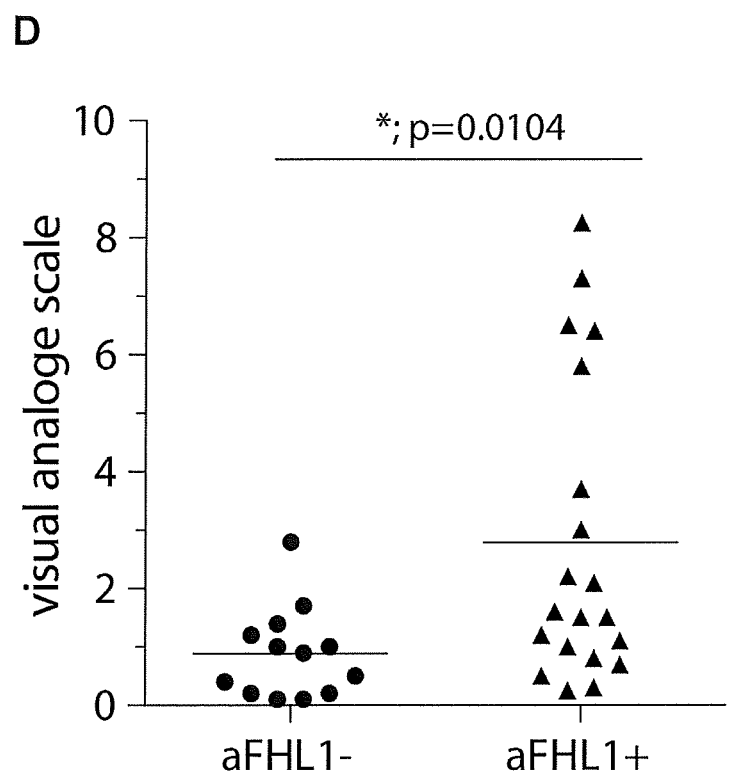

FIG. 4: Presence of anti-FHL1 autoantibodies is associated with a high disease severity.

(A) Statistical analysis revealed that anti-FHL1$^+$ compared to anti-FHL1$^-$ patients had a higher incidence of developing dysphagia (p=0.002; Fischer's exact test), distal muscle weakness (p=0.022), clinical atrophy (p=0.007), fiber necrosis (p=0.042) and connective tissue/fat replacement (p=0.002). (B) Anti-FHL1$^+$ patients compared to a-FHL1$^-$ patients had a higher incidence of showing HLA DRB1*03/13 genotype (p=0.0228; Chi-square test). (C) Patients having anti-FHL1 autoantibodies were scored for disease severity and compared to myositis patients without anti-FHL1 autoantibodies. Scoring for disease severity was done using a scoring catalog examining disease outcome from last patient visit at the clinic. (Scoring: Remission without treatment: 0; Remission (high MDI VAS): 0.5; —Remission with treatment: 1; Low disease activity with treatment: 2; Moderate disease activity: 3; Refractory/progressive disease, —Persistant, therapyresistant 4; MDI VAS>50: 4.5; MDI VAS>70: 5) (D) Hematoxylin/eosin and Gomori trichrome stained muscle sections of 20 patients having anti-FHL1 autoantibodies were examined for histopathology and compared to gender-, age- and diagnosis- (PM, DM, IBM, n=13) matched patients negative for anti-FHL1 autoantibodies. Scoring was done using a 0-10 cm visual analog scale (VAS). Scoring in (C) and (D) was done blindly regarding FHL1 autoantibody status; statistics for (C) and (D): two-tailed Mann Whitney test, each data point represents one individual and horizontal bars indicate mean values FIG. 5. A higher amount of two additional lower molecular weight bands can be detected in anti-FHL1$^+$ muscle biopsy lysates compared to HC and anti-FHL1$^-$ tissue, whereas mRNA expression for the three major isoforms is equal.

(A) Lysates were generated from muscle tissue biopsy material of patients with or without anti-FHL1 autoantibodies as well as from healthy muscle and immunoblotted with commercially available anti-FHL1 antibody. Immunoblotting with GAPDH was used as loading control. (B) The three major bands detected by immunoblot were quantified using Quantity One 1-D Analysis software and normalized to loading control GAPDH by calculating FHL1-band$_{Mean\ Value-intensity}$/GAPDH-band$_{Mean\ Value-intensity}$. (C) mRNA was extracted from muscle biopsy material from anti-FHL1$^+$ (n=13) and anti-FHL1$^-$ patients (n=13) as well as HCs (n=12) and transcribed into cDNA. FHL1 expression on mRNA level was analyzed by TaqMan PCR using specific primers for amplification of isoform A, B and C. Each data point represents one individual and horizontal bars indicate mean values.

Figure 6:
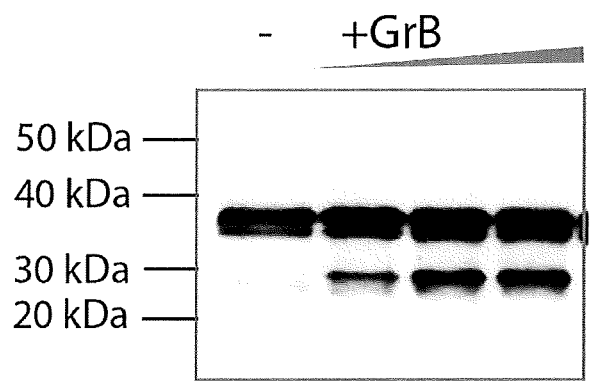
Figure 6:
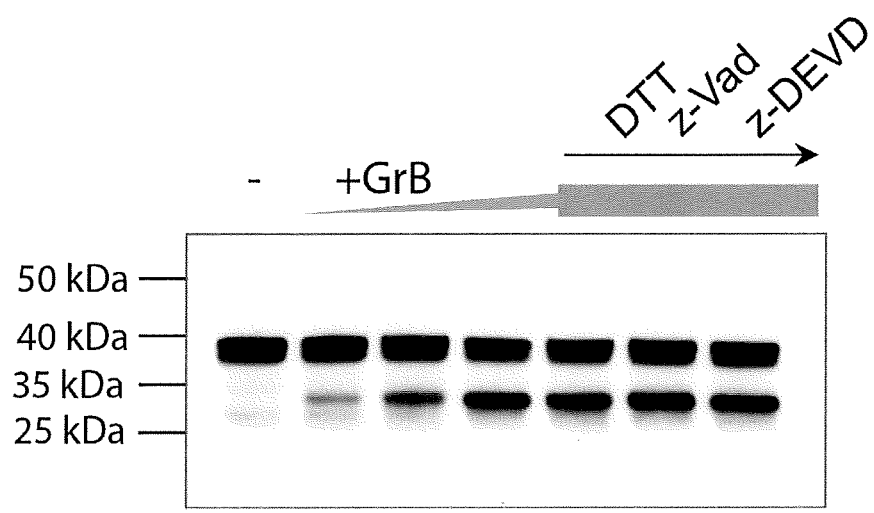
Figure 6:
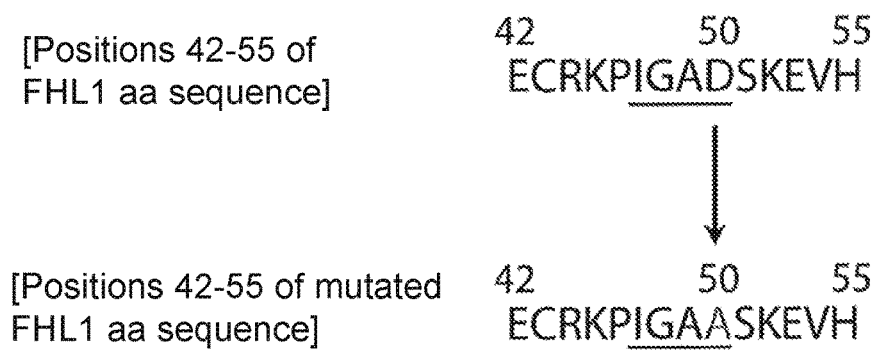
Figure 6:
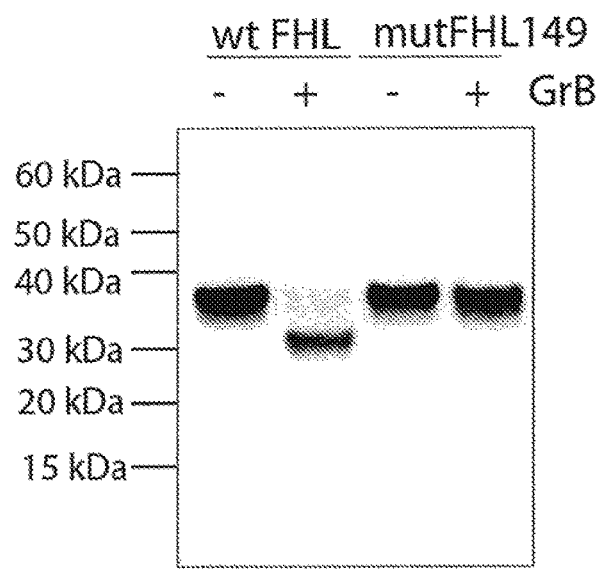

FIG. 6: FHL1 protein is a substrate of granzyme B.

(A) FHL1 susceptibility to granzyme B cleavage was demonstrated by performing a cleavage assay using lysates from cultured skeletal muscle cells and increasing concentrations of recombinant granzyme B (50, 100, 250U). (B) The cleavage assay was performed with increasing concentrations of granzyme B and if indicated, DTT (5 mM), z-Vad (500 nM) or z-DEVD (500 nM) was added. The results for the cleavage assay are representative for 5 independent experiments. In addition, also recombinant His-tagged FHL1 (C), commercially available FHL1 protein (Origene) (D) and FHL1-MaBP fusion protein (E) were submitted to an in vitro cleavage assay with granzyme B. For the latter, the immunoblot was developed with both, an antibody binding to N terminus and an antibody binding to C terminus indicating that the cleavage site is located near the N terminus of the protein. The cleavage site was according to granzyme B tetrapeptide specificity and size of the cleavage fragment predicted to be IGAD with D at amino acid position 50 (F). Using site directed mutagenesis, the cleavage site was mutated and in-vitro-transcription-translation (IVTT) expressed wildtype or mutated FHL1 were incubated with granzyme B or left untreated and analyzed by western blot (G).

Figure 7:
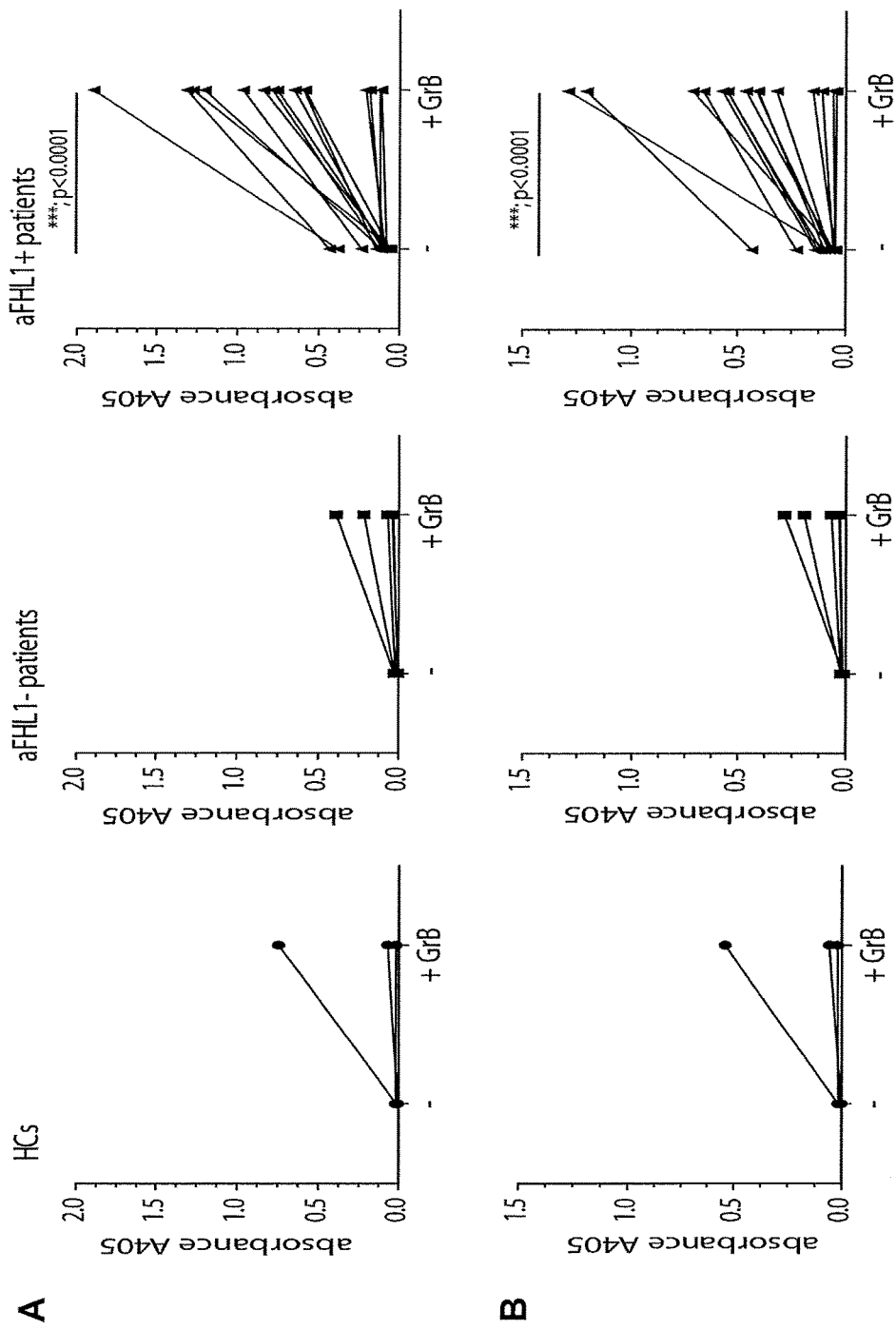
Figure 7:
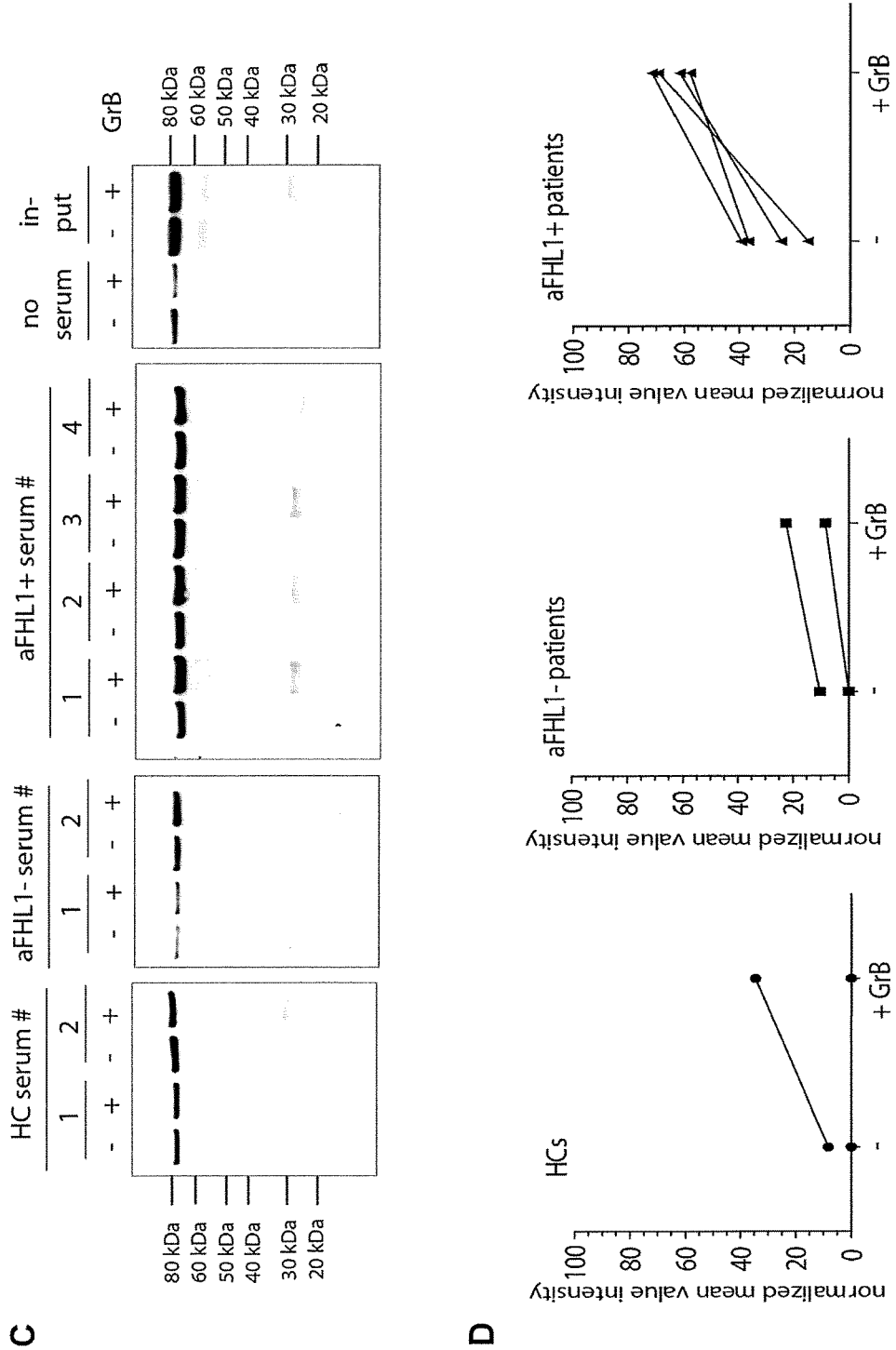

FIG. 7: Granzyme B cleavage increases immunoreactivity of FHL1. His-tag FHL1 (A) or FHL1-MaBP fusion protein (B) was submitted to an in vitro cleavage assay with granzyme B or left untreated and used as antigen in ELISA experiments. Sera from previously identified anti-FHL1$^+$ (n=15) or anti-FHL1$^-$ patients (n=3) as well as HCs (n=2) were analyzed for immunoreactivity. Statistical analysis was done using Wilcoxon matched-pairs signed rank test. (C) Cleaved or uncleaved FHL1-MaBP fusion protein was immunoprecipitated using anti-FHL1$^+$ (n=4) or anti-FHL1$^-$ (n=2) as well as HC sera (n=2); controls: IP without adding serum and input (sample before IP). (D) Intensities of the signals were quantified using Quantity One 1-D Analysis software and normalized by calculating band IP$_{signal\ intensity\ area}$−band IP no serum$_{signal\ intensity\ area}$.

DETAILED DESCRIPTION OF THE INVENTION

Screening a cDNA expression library is a powerful technique that may identify previously uncharacterized antigens from patients' sera containing antibodies. In this study, this methodology was used and a human muscle-specific cDNA expression library was screened with sera from myositis patients, which allowed the identification of a strongly reactive clone encoding FHL1. By enzyme-linked immunosorbent assay (ELISA) it was possible to further confirm this reactivity and to measure IgG specific to FHL1 in around 25% of patients with IIM. In contrast, patients suffering from other autoimmune diseases including rheumatoid arthritis (RA) or primary Sjögren's Syndrome (pSS) were tested mostly negative for reactivity to FHL1. In IIM, presence of anti-FHL1 autoantibodies was associated with dysphagia, distal muscle weakness, clinical atrophy, muscle fiber necrosis and connective tissue/fat replacement of the muscle. Moreover, anti-FHL1+ patients more often develop vasculitis and show HLA DRB1*03/13 genotype. Confocal microscopy analysis revealed that, compared to a homogenous expression in healthy muscle, FHL1 protein in IIM muscles shows a disturbed expression pattern similar to that observed in genetic muscular disorders caused by FHL1 mutation (Schessl ibid). Moreover, the present inventors provide evidence that FHL1 is highly susceptible to cleavage by granzyme B, which might mediate its autoantigenic properties, lead to a break of tolerance and initiate formation of anti-FHL1 autoantibodies. Importantly, those autoantibodies are indicators of disease severity in particular affecting functionality of the skeletal muscle qualifying them as biomarkers for a poor prognosis in this disease.

In one aspect, the present invention provides methods for the diagnosis of autoimmune muscle diseases. The methods comprise detection of autoantibodies specifically binding to FHL1 in a sample obtained from a subject. The methods can be used for assessing the subject's risk of developing an autoimmune muscle disease. The methods can further comprise assessing the level of autoantibodies specifically binding to FHL1 in the sample and in a control sample, and determining that the subject is likely to develop an autoimmune muscle disease, or is suffering from an autoimmune muscle disease, when the level of autoantibodies specifically binding to FHL1 in the sample is greater than the autoantibodies specifically binding to FHL1 in the control sample.

The methods can be used for assessing the severity and/or the prognosis of the autoimmune muscle disease. The methods can further comprise assessing the level of autoantibodies specifically binding to FHL1 in the sample and comparing it to the level of autoantibodies specifically binding to FHL1 in control samples obtained from patients where the severity and/or the prognosis of the autoimmune muscle disease has been documented, and determining the severity and/or the prognosis of the autoimmune muscle disease in the subject.

The autoimmune muscle disease can be an idiopathic inflammatory myopathy (myositis). Preferably, the autoimmune muscle disease is characterized by the presence of autoantibodies specific to FHL1.

The subject can be a human. The sample can be a blood sample, such as serum or plasma.

Antibodies specifically binding to FHL1 can be detected using an immunoassay, such as ELISA, or RIA, by surface plasmon resonance, or electrochemiluminescence.

The "immunoassay" used to detect autoantibodies specifically binding to FHL1 according to the invention may be based on standard techniques known in the art. In a preferred embodiment the immunoassay may be an ELISA.

ELISAs are generally well known in the art. In a typical ELISA the FHL1 antigen is immobilised on a solid surface (e.g. the wells of a standard microtiter assay plate, or the surface of a microbead or a microarray) and a sample comprising the sample to be tested for the presence of autoantibodies specifically binding to FHL1 is brought into contact with the immobilised antigen. Any autoantibodies of the desired specificity present in the sample will bind to the immobilised antigen. The bound antibody/antigen complexes may then be detected using any suitable method. In one preferred embodiment, a labelled secondary anti-human immunoglobulin antibody, which specifically recognises an epitope common to one or more classes of human immunoglobulins, is used to detect the antibody/antigen complexes. Typically the secondary antibody will be anti-IgG or anti-IgM. The secondary antibody is usually labelled with a detectable marker, typically an enzyme marker such as, for example, peroxidase or alkaline phosphatase, allowing quantitative detection by the addition of a substrate for the enzyme which generates a detectable product, for example a coloured, chemiluminescent or fluorescent product. Other types of detectable labels known in the art may be used.

In a radioimmunoprecipitation assay the antigen is typically produced in vitro by in vitro transcription of a specific plasmid containing the cDNA sequence of FHL1 or a fragment thereof with suitable promotors, e.g. T7, T3 and SP-6, followed by in vitro translation in the presence of a components from a reticulocyte lysate and a radioactive amino acid, e.g. S35-methionine. The resulting radioactive proteins are then incubated with patient sera, the antibodies collected by Protein A or G bound to a matrix, antibodies against IgG and or IgM and or IgA, collected, washed and the bound radioactivity analysed.

A second aspect of the present invention provides FHL1 and/or a peptide fragment derived from FHL1 for use in the treatment of autoimmune muscle diseases.

In one embodiment, the method comprises administering a pharmaceutical composition comprising a therapeutically active amount of FHL1 or a peptide fragment derived from FHL1 to a patient in need of such treatment.

Accordingly, the second aspect of the present invention provides a pharmaceutical composition comprising therapeutically effective amount of FHL1 or a peptide fragment derived from FHL1 for use in the treatment of autoimmune muscle diseases. The pharmaceutical composition can further comprise an adjuvant and/or other immunostimulatory molecules or cells.

Put another way, the second aspect of the present invention provides for use of FHL1 or a peptide fragment thereof for the manufacture of a pharmaceutical composition for treatment of autoimmune muscle diseases.

In one embodiment, the invention provides a method for the treatment of an autoimmune muscle disease which comprises administering a therapeutically active amount of FHL1 and/or a peptide fragment derived from FHL1 to a patient in need of such treatment.

In one embodiment, use of FHL1 or a peptide fragment thereof for the treatment of autoimmune muscle diseases according to the second aspect of the invention, is intended to evoke an immune response to FHL1 in the patient in need of such treatment. The immune response preferably induces tolerance to FHL1 in the patient. The immune response can be a B-cell response and/or a T-cell response. The fragment of FHL1 is preferably an immunological active fragment, an epitope.

The pharmaceutical composition comprising a therapeutically active amount of FHL1 or a peptide fragment thereof preferably also comprises an adjuvant. Adjuvants include any compound or compounds that act to increase an immune response to FHL1 antigen, thereby reducing the quantity of antigen necessary in the vaccine, and/or the frequency of administration necessary to generate a protective immune response. Adjuvants can include for example, emulsifiers, muramyl dipeptides, pyridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides, natural or synthetic lipids binding to the CD1d molecule expressed on NKT cells, and combinations thereof. Preferably, the adjuvant is an adjuvant that acts to promote tolerance to FHL1, i.e. a tolerogenic agent. The tolerogenic agent can be an antibody, e.g. anti-CD4, anti-CD3, anti-CD25, anti-CD28, anti-PD1, anti-BTLA, anti-B7, anti-ICOS, anti-CTLA, anti-CD40, anti-CD40L, anti-CD99, anti-CD2, anti-LFA3, anti-CD27, anti-CD70, anti-DC8, anti-OX40, anti-OX40L, anti-LFA-1, anti-CD11a, anti-ICAM1, anti-CD26, anti-CD44, anti-CD137, CTLA4-Ig, anti-MHC class II and anti-MHC class I. The tolerogenic agent can be a bacterial toxin, e.g. cholera toxin sub unit B (CTB), or mutants of cholera toxin subunit A1 (CTA1)

Definitions

The phrases "an antibody recognizing an antigen" and "an antibody specific for an antigen" are used interchangeably herein with the term "an antibody which binds specifically to an antigen."

The terms "inflammatory muscle disease", "myositis" and "idiopathic inflammatory myopathy" are used interchangeable herein is intended to include polymyositis (PM), dermatomyositis (DM), inclusion body myositis (IBM), juvenile dermatomyositis (JDM), juvenile polymyositis (JPM) and immune mediated necrotizing myopathy.

The term "FHL1" as used herein is intended to include isoform A, also known as isoform 1, FHL1, FHL1A, and SLIM; isoform B, also known as isoform 2, FHL1B, and SLIMMER; isoform C, also known as isoform 3, and FHL1C; isoform 4; and isoform 5.

The term "a peptide fragment derived from FHL1" as used herein is intended to include any peptide comprising or consisting of an amino acid sequence derived from FHL1. A peptide fragment derived from FLH1 can preferably comprise an autoimmune epitope. The autoimmune epitope can be an epitope generated proteolytic cleavage of FHL1.

Full-length FHL1 or one or more peptides fragment derived from FHL1 can be used as antigen in the detection of autoantibodies specifically binding to FHL1.

The amino acid sequence of FHL1 can be found in GenBank Accession No. U29538 or SwissProt/UniProt Accession No. Q13642 (FHL1_HUMAN).

EXAMPLES

1. Material and Methods

Patient Material.

Sera were obtained from myositis patients (n=141, age=56.97 years, 67.42% Females, DM n=0.49, PM n=66, IBM n=12, JDM n=5), from the Rheumatology unit, Karolinska University Hospital, Stockholm, Sweden, and compared to gender- and age-matched healthy controls (n=126, age=56.2 years, 66.7% Females) as well as patients from the same clinic diagnosed as MCTD (n=19), RA (n=67, gender- and age-matched to anti-FHL1+ patients), pSS (n=35; gender- and age-matched to anti-FHL1+ patients), SLE (n=33; gender- and age-matched to anti-FHL1+ patients), SSc (n=32, gender- and age-matched to anti-FHL1+ patients) and patients with genetically caused neuromuscular diseases (n=9). In addition, sera from a myositis cohort from the Institute of Rheumatology and Department Rheumatology, Charles University in Prague, Czech Republic, were examined (n=129) and compared to healthy control sera (n=81). Myositis patients fulfilled the diagnostic criteria for definite or probable PM or DM (Bohan & Peter. *Polymyositis and dermatomyositis (second of two parts)*. N Engl J Med 1975, 292(8):403-407; Bohan & Peter. *Polymyositis and dermatomyositis (first of two parts)*. N Engl J Med 1975, 292(7): 344-347) or IBM (Griggs et al. *Inclusion body myositis and myopathies*. Ann Neurol 1995, 38(5):705-713). In addition, muscle biopsies from 11 myositis patients and 4 healthy controls were analyzed by microscopy and/or Western Blot. All experiments were approved by the local ethics committee at Karolinska Insitutet and Institute of Rheumatology, Prague, and all patients gave informed consent.

Clinical and Laboratory Data

For 132 out of 141 patients (anti-FHL1+ n=33; anti-FHL1− n=99), a detailed amount of clinical data and laboratory data from patient records at Karolinska University Hospital and from the web-based SweMyoNet and Euromyositis registries with long-term follow up was accessible. In addition to demographic data and information on disease duration, progress of disease, and heredity for neuromuscular or inflammatory, rheumatic disease, data on the following symptoms and signs were retrieved: malignancy, patterns of muscle weakness, myopathic electromyogram (EMG), clinical atrophy, skin manifestations (Gottron's papules, Heliotrope rash, mechanic's hands, Raynaud's phenomenon, calcinosis shawl sign, ulceration and V-sign), interstitial lung disease, dysphagia, heart effect, arrhythmia, heart failure, myocarditis/cardiomyopathy, thrombosis/embolism, vasculitis, arthritis/synovitis, laboratory measures (highest serum levels of creatine kinase (CK), alanine aminotransferase (ALAT), aspartate aminotransferase (ASAT) and lactate dehydrogenase (LD) found in the records or registries, and C-reactive protein (CRP) and sedimentation rate (SR) at diagnosis), and clinical measurements such as manual muscle test-8 (MMT8) and health assessment questionnaire (HAQ) at the latest visit to the clinic. In addition, data on muscle biopsy features including inflammation, endomysial inflammation, perivascular inflammation, MHC class I expression on sarcolemma, fiber necrosis, perifascicular atrophy, rimmed vacuoles in non-necrotic fibers, invasion of non-necrotic fibers, fiber degeneration/regeneration, connective tissue/fat and mitochondrial changes, were collected. Data on autoantibody profiles of the patients were retrieved (antinuclear antibodies (ANA), anti-Jo-1, anti-Ro52, anti-SRP, anti-U1RNP antibodies). For examination of disease severity with a special focus on muscle involvement, the following scoring catalog considering the overall outcome and including the physician's International Myositis Assessment & Clinical Studies Group (IMACS) myositis damage index (MDI) was developed. VAS score: Remission without treatment=0; Remission without treatment with MDI VAS>20=0.5; remission with treatment=1; low disease activity with treatment=2; moderate disease activity=3; refractory, progressive disease, persistent, therapy-resistant=4 and MDI-Vas>50=4.5 and MDI-VAS>70=5, respectively. Scoring was done blindly regarding presence of anti-FHL1 autoantibodies for the last recorded visit by the responsible physician.

Immunoscreening of the Muscle Specific cDNA Library.

A commercially available muscle cDNA library (Uni-ZAP XR Premade Library) was screened with sera from 3 patients with IIM. The sera were selected on the basis of PM, DM and DM with an associated malignancy. After four immunoscreenings, clones were isolated and subjected to PCR amplification as well as DNA sequencing. The obtained sequence data were compared to available databases by the Basic Local Alignment Search Tool (BLAST) searches.

Cloning and Expression of Recombinant Proteins.

Human FHL1 CDS was amplified from FHL1 Human cDNA ORF clone (transcript variant 2; NM_001449; origene) introducing EcoRI (5'-CAA CAA GAA TTC ATG GCG GAG AAG TTT GAC TG-3') (SEQ ID NO:1) and SalI (5'-CAA CAA GTC GAC TTA CAG CTT TTT GGC ACA G-3') (SED ID NO:2) restriction sites and ligated into the multiple cloning site of pTNT™ vector (Promega). Based on pTNT™ vector, FHL1 ORF was subcloned into either pMAL-cRI (New England Biolabs) or pET-28a (Novogen) expression vectors and proteins with a Maltose-Binding protein (MaBP)- and a His-tag, respectively, were expressed in BL21 Escherichia coli cells. Wildtype MaBP was used as control. Full-length proteins were purified on amylose columns (for MaBP fusion proteins, NEB) and Ni-NTA columns (for His-tag proteins, Pierce), respectively, according to manufacturer's instructions. In some experiments a commercially available recombinant FHL1 protein (Origene, transcript variant 2, GenBank accession: NM_001449) was used.

ELISA for Detection of Antibodies Against FHL-1.

ELISA was performed as previously described (Salomonsson et al. *A serologic marker for fetal risk of congenital heart block.* Arthritis Rheum 2002, 46(5):1233-1241). Briefly, maxisorb 96-well plates (442404, Nunc) were coated with 1 µg recombinant FHL1-MaBP or FHL1-His tag full-length protein per well diluted in carbonate buffer, pH 9.6 overnight at 4 degrees. Plates were blocked with phosphate buffered saline (PBS)/0.05% Tween20/5% milk powder, and sera were tested at a dilution of 1:500 in PBS/Tween/1% milk powder. Bound antibodies were detected by alkaline-phosphatase (AP)-conjugated anti-human IgG (DAKO). Phosphatase substrate tablets (Sigma) dissolved in diethanolamine buffer, pH 9.6, were used as substrate. Absorbance was measured at 405 nm (A405). For ELISAs with FHL1-MaBP fusion protein, all sera were tested for reactivity to MaBP fusion partner. In general, OD values for MaBP only ELISAs were <0.2. Absorbances obtained from ELISAs with FHL1-MaBP fusion protein were in addition normalized to reactivity to MaBP alone by subtracting A405 measured to MaBP from A405 measured to FHL1-MaBP fusion. In some experiments, ELISAs were performed with FHL1 cleaved by granzyme B.

Immunoblot.

Immunoblot was performed with a monoclonal anti-FHL1 antibody (ab76912, Abeam), mouse monoclonal anti-GAPDH antibody (398600, Invitrogen) or rabbit monoclonal anti-GAPDH antibody (14C10, Cell Signaling Technology), followed by incubation with horseradish peroxidase (HRP)-coupled anti-mouse (DAKO) or anti-rabbit (DAKO) secondary antibodies. In some experiments patient sera were used as primary antibody-source; followed by incubation with HRP-coupled anti-human IgG (DAKO). Individual bands were visualized with enhanced chemiluminescence (GE Healthcare). Quantification was done Quantity One 1-D Analysis software.

HLA Genotyping.

HLA typing was performed using sequence-specific primer-polymerase chain reaction (PCR) (DR low-resolution kit; Olerup SSP, Saltsjöbaden, Sweden), and the PCR products were loaded onto 2% agarose gels for electrophoresis. An interpretation table was used to determine the specific genotype according to the recommendations of the manufacturer.

Histopathological Examination.

Muscle biopsy sections stained by hematoxylin/eosin and Gomori from 20 anti-FHL1$^+$ patients and from 13 gender-, age- and diagnose-(PM; DM and IBM) matched antibody negative patients were assessed by an experienced muscle pathologist for pathogenic changes. Scoring was done blindly regarding status of anti-FHL1 autoantibody positivity. Characteristics examined included muscle fiber atrophy, fibrosis, necrosis/degeneration, regeneration, presence of inflammatory infiltrates, internal nuclei, variation of fiber size, and rimmed vacuoles. Based on these features, the overall severity of histopathology was scored with a visual analog scale system (0-10 cm).

Immunofluorescense/Confocal Microscopy.

Muscle biopsies were frozen in isopenthane prechilled by liquid nitrogen, sectioned into 7 µm sections, formalin fixed and stored at −70° C. until processing. Formalin-fixed muscle tissue sections were permeabilized with 0.1% saponin and stained with monoclonal mouse anti-human FHL1 antibody (ab76912, Abeam) followed by Alexa Fluor 594-conjugated anti-mouse antibody (Invitrogen). In addition, sections were incubated with rabbit polyclonal anti-laminin followed by Alexa Fluor 488-conjugated anti-rabbit antibody (Invitrogen). Nuclei were counterstained with DAPI (Roche), and sections were mounted in Fluoromount-G (SouthernBiotech). Images were acquired using a Leica TCS SP5 and acquisition was performed using a 40× oil objective. A z-dimension series was taken every 0.2 µm. Images were analyzed with the ImageJ software.

mRNA Expression Analysis.

RNA was obtained from muscle biopsies from non-myositis affected individuals and myositis patients positive or negative for anti-FHL1 autoantibodies. The RNeasy® Fibrous Tissue Mini Kit (Qiagen, Hilden, Germany) was used for the RNA extraction. Samples were stored at −80° C. prior to cDNA synthesis, which was performed with an iScript cDNA synthesis kit following the manufacturer's protocol (Bio-Rad, Hercules, Calif., USA).

Pre-designed and custom TaqMan® assays from Life Technologies were used to interrogate the transcript expression levels of three well-established splice forms of FHL1 (reviewed by Shathasivam et al. *Genes, proteins and complexes: the multifaceted nature of FHL family proteins in diverse tissues.* J Cell Mol Med 2010, 14(12):2702-2720) as represented by their RefSeq accessions: FHL1A: NM_001449.4 (full-length); FHL1B: NM_001159702.2; FHL1C: NM_001159703.1. The detection of the transcript FHL1B was performed using the predesign real-time gene expression assay Hs00938359_g1 (Applied Biosystems, Life Technologies, Europe), with a probe spanning exons 7-8; context sequence reporter 5'-FAM*-CTCCTCGAGGC-CCGGGTTTGGTAAA-NFQ**-3', (SEQ ID NO:3). Two custom TaqMan® assays were designed to evaluate the expression of FHL1A and FHL1B transcripts. For the FHL1A the context sequence spanning exons 6-8: 5'-FAM*-ACCCCATCACTGGGTTTGGTA-NFQ**-3' (SEQ ID NO:4); and for the FHL1C the probe spanning exons 5-8: 5'-FAM*-AGTGCAACAAGGGTTTGG-NFQ**-3' (SEQ ID NO:5). For primer design the on-line Custom TaqMan® Assay Design Tool from Applied Biosystems was used. The experiment was set at least in triplicates. Three non-template controls were included in each experiment. Expression measurements were made using the delta-delta relative quantification method (ΔΔ Cycle threshold) with QuantStudio™ 6 and 7 Flex Real-Time PCR System and ExpressionSuite Software Version 1.0.4. ZNF592 gene was used as an endogenous reference control (predesign assay Hs00206029_m1) which ΔCt was subtracted from each individual measurement. The mean ΔCt values for controls were used as a calibrator.

Cleavage Assays of Muscle Lysates.

Cultured skeletal muscle cells were lysed in 10 mM Hepes, 2 mM EDTA, 1% NP-40 including Leupeptin, Antipain, Pepstatin A and PMSF. If indicated the reaction was done in presence of 5 mM Dithiothreitol (DTT, Sigma-Aldrich); 500 nM z-Vad-FMK or 500 nM z-DEVD-FMK (both from BD Pharmingen). In some experiments 100 ng purified recombinant protein was used as substrate. Human recombinant granzyme B (Enzo Life Sciences) was used in different concentrations. The cleavage was done for 1.5 hr at 37° C. and stopped by adding SDS sample buffer and boiling. The reaction was loaded on a SDS PAGE and blotted to Nitrocellulose Membrane. Detection was done with a mouse monoclonal anti-FHL1 antibody (ab76912, Abcam) or a goat polyclonal anti-FHL1 (ab23937, Abcam). The granzyme B cleavage site in FHL1 was confirmed by cloning FHL1 CDS in pTNT plasmid (Promega) and mutating aspartic acid (D) at amino acid position 50 to Alanin (A) using site directed mutagenesis (Agilent). Primers used for mutagenesis PCR were a149c antisense (5'-cacctcettggag-gccgcaccgatggg-3') (SEQ ID NO:6) and a149c sense (5'-cccatcggtgcggcctccaaggaggtg-3') (SeQ ID NO:7). Wild type and mutated protein were expressed by in vitro transcription/translation (IVTT; Promega) and cleaved with granzyme B. The reaction was loaded on a PAGE, and immunoblot was developed using monoclonal anti-FHL1 antibody (ab76912, Abcam).

Immunoprecipitation.

For Immunoprecipitation, recombinant FHL1 fusion protein was cleaved by granzyme B or left untreated. To 500 µl of protein solution, 2.5 µl sera were added and the mixture was incubated for 2 hours at 4° C. Immunoprecipitation was performed using magnetic ProteinG beads according the manufactures instructions (Miltenyi Biotech). The eluted immunoprecipitate was analyzed by SDS PAGE and subsequent immunoblot using monoclonal anti-FHL1 (ab76912, Abcam). Quantification of the signals was done with ImageJ software. Signal intensities of not cleaved and cleaved FHL1 bands were summated and the intensity of the bands detected in IP samples without any serum (background) was subtracted.

Statistical Analysis.

The significance of differences in the performed ELISAs, the clinical outcome score, the histopathology score as well as grip strength and weight measurements in the animal experiments was calculated by Mann-Whitney test. The significance of differences between anti-FHL$^+$ and anti-FHL$^-$ patients regarding associations with clinical parameters was calculated by rank sum test for continuous variables, and by Fischer's exact test or Pearson's chi-square test for categorical variables. The programs Stata (StatCorp, College Station, Tex., USA) or GraphPad Prism 6.0 were used for data management and statistical analyses. P values less than or equal to 0.05 were considered significant.

2. Results

Identification of Anti-FHL1 Autoantibodies by Immunoscreening of a Muscle Specific cDNA Library.

In order to identify genes encoding putative muscle-specific autoantigens, a muscle cDNA library was immunescreened with serum from 3 patients with established myositis, one with PM, the second one with DM, and the third one diagnosed as paraneoplastic DM. One of those patients was tested positive for having autoantibodies directed against the histidyl-tRNA synthetase (Jo1). It was possible to identify several clones with cDNA insertion of this well-known myositis-specific autoantigen (Nishikai & Reichlin. *Heterogeneity of precipitating antibodies in polymyositis and dermatomyositis. Characterization of the Jo-1 antibody system*. Arthritis Rheum 1980, 23(8):881-888) making it a good internal control for the used methodology. Besides detecting histidyl-tRNA synthetase clones, other strongly reactive clones were identified, which coded for muscle tissue specific proteins. One of those clones had an 843 base pair open reading frame and a predicted amino acid sequence of 281 residues that had 100% identity with FHL1 (four-and-a-half LIM domain 1). Most importantly, FHL1 missense mutations have been linked to a couple of rare congenital myopathies (Schessl ibid; Windpassinger ibid; Gueneau ibid; Quinzii et al. *X-linked dominant scapuloperoneal myopathy is due to a mutation in the gene encoding four-and-a-half-LIM protein 1*. Am J Hum Genet 2008, 82(1):208-213). Since this might indicate an important role of FHL1 in muscle diseases, it was selected for further analysis.

Anti-FHL1 Autoantibodies are Detected at High Frequencies in Patients with Established Myositis.

To validate the presence of autoantibodies against FHL1 in patients with myositis and examine the prevalence of those autoantibodies in this disease, an ELISA was established to detect IgG specific to FHL1 in serum. FHL1 coupled to the Maltose-Binding protein (MaBP) was used as antigen, and in addition, ELISAs with only MaBP as antigen were performed as controls. The latter showed either no or only small reactivity demonstrating the specificity of the reaction. 141 patients with IIM were examined and compared serum reactivity with that of gender- and age-matched healthy controls. Myositis patients showed a highly significant increase in appearance of autoantibodies directed against FHL1 (FIG. 1A). Examining healthy controls allowed us to determine a cut-off value by that anti-FHL1 negative and anti-FHL1 positive (anti-FHL1$^+$) patients could be differentiated. In total 35 of the 141 patients (24.8%) were identified with a positive reactivity against FHL1 (FIG. 1B). Positive reaction against FHL1 was subsequently confirmed by another ELISA using a recombinant FHL1 protein with a His-tag (FIG. 1C) and a Western Blot using recombinant FHL1-MaBP fusion protein (FIG. 1D). The Western Blot also verified no reactivity against FHL1 in healthy control sera and no reactivity of sera from anti-FHL1 positive patients against MaBP (FIG. 1D). The presence of anti-FHL1 autoantibodies could also be confirmed an independent cohort of 129 myositis patients from Czech Republic; here 31 (24%) of patients were identified as being positive for autoantibodies to FHL1 (FIG. 2). Interestingly, 3 of 81 (3.78%) of the gender- and age-matched healthy controls showed positivity for anti-FHL1 autoantibodies.

Anti-FHL1 Autoantibodies are Myositis Specific.

Autoantibodies found in myositis can be divided into myositis-specific autoantibodies that can be detected exclusively in inflammatory myopathies and in myositis-associated autoantibodies, which are frequently observed in other auto-inflammatory diseases like (SLE), (SSc) or rheumatoid arthritis (RA) (Targoff. *Autoantibodies in polymyositis*. Rheum Dis Clin North Am 1992, 18(2):455-482). Next it was investigated whether autoantibodies directed to FHL1 are falling into the group of myositis-specific or associated autoantibodies and compared the presence of anti-FHL1 autoantibodies in patients with inflammatory myopathies and other autoimmune diseases including mixed-connective tissue disease (MCTD), RA, pSS, SLE and SSc. When possible sera were selected from patients that were gender- and age matched to anti-FHL1+ myositis patients. The majority of sera from patients with other autoimmune diseases did not show reactivity to FHL1 (FIG. 3). In addition, sera from patients with genetically caused neuromuscular disorders with muscle weakness were analyzed. Here, no anti-FHL1 specific autoantibodies could be detected (FIG. 3) showing that the autoantibodies are not formed as bystanders because of excessive destruction of muscle tissue.

Presence of Anti-FHL1 Autoantibodies is Associated with Dysphagia as Well as High Muscle Disease Severity and Histopathology.

For 132 out of 141 patients (anti-FHL1+ n=33; anti-FHL1- n=99), detailed clinical data with long-term follow up was available (descriptive characteristics of the cohorts are displayed in Table 1). FHL1 autoantibodies were detectable in all three major subtypes of myositis. Specifically, 19 of 33 anti-FHL1+ patients were diagnosed with PM (58%), 10 with DM (30%), one was diagnosed with Juvenile DM (3%), and 3 of 33 patients had IBM (9%). To clinically characterize the autoantibody positive patients, possible associations of clinical features in inflammatory myopathies with anti-FHL1 reactivity were analyzed. Anti-FHL1+ and anti-FHL1- patients were compared regarding clinical muscle variables, different extra-muscular involvement, muscle biopsy features, laboratory measures, and presence of additional autoantibodies (Tables 2, 3 and 4). It was found that several clinical features were strongly associated with presence of anti-FHL1 autoantibodies (Table 2). Patients having anti-FHL1 autoantibodies developed more often dysphagia compared to patients without anti-FHL1 autoantibodies (28 of 33 (85%) compared to 52 of 96 (54%), p=0.002, positive predictive value=85%) (Table 2, FIG. 4A). Dysphagia is a disease parameter that is associated with a high severity of myositis (Horowitz et al. *Abnormalities of gastric and esophageal emptying in polymyositis and dermatomyositis*. Gastroenterology 1986, 90(2):434-439). Highly significant associations were further found between presence of anti-FHL1 autoantibodies and distal muscle weakness (p=0.022, positive predictive value=94%), clinical muscle atrophy (p=0.007, positive predictive value=66%), vasculitis (p=0.008, positive predictive value=18%), as well as fiber necrosis (p=0.022, positive predictive value=94%) and connective tissue replacement of muscle tissue (p=0.002, positive predictive value=44%) as evident by muscle biopsies (Table 2, FIG. 4A). These associations indicate a link between positivity for anti-FHL1 autoantibodies and disease severity in particular affecting skeletal muscle. No associations between anti-FHL1 autoantibody positivity and any of the laboratory measures analyzed or presence of other autoantibodies were found (Tables 3 and 4). In addition, the statistical analysis revealed an association between anti-FHL1 positivity and vasculitis (Table 2). Moreover, the HLADRB1*03/13 genotype was over-represented in patients with autoantibodies to FHL1 compared to anti-FHL1-patients; 7 of 33 anti-FHL1+ (21.2%) patients were detected to have this haplotype whereas in the anti-FHL1- patients it was only 6 of 88 (6.8%, Fisher's exact test p=0.04) (FIG. 4B).

TABLE 1

Descriptive characteristics

| Variable | aFHL1+ (n = 33) | aFHL1- (n = 99) | Total (n = 132) | P value |
|---|---|---|---|---|
| Gender, n (%) | | | | |
| Female | 26 (79) | 63 (64) | 89 (67) | 0.135 |
| Male | 7 (21) | 36 (36) | 43 (33) | |
| Diagnosis, n (%) | | | | |
| PM | 19 (58) | 47 (47) | 66 (50) | |
| DM | 10 (30) | 39 (39) | 49 (37) | 0.812 |
| IBM | 3 (9) | 9 (9) | 12 (9) | |
| JDM | 1 (3) | 4 (4) | 5 (4) | |
| Ethnicity, n (%) | | | | |
| Caucasian | 30 (91) | 95 (96) | 125 (95) | 0.366 |
| Other | 3 (9) | 4 (4) | 7 (5) | |
| Insidious progress of disease, n (%) | 22 (71) | 64 (80) | 86 (77) | 0.320 |
| Malignancy, n (%) | 6 (18) | 26 (27) | 32 (24) | 0.482 |
| Age at first symptom, median (IQR), years | 49 (30-57) | 49 (39-61) | 49 (39-61) | 0.604 |
| Age at diagnosis, median (IQR), years | 50 (30-57) | 50 (40-63) | 50 (40-62) | 0.652 |
| Age at serum test, median (IQR), years | 59 (52-68) | 61 (48-67) | 60 (49-68) | 0.827 |
| Disease duration, median (IQR), years | 8 (3-12.5) | 5 (1-8) | 5 (2-10) | 0.058 |
| Heredity for neuromuscular diseases, n (%) | 0 (0) | 2 (4) | 2 (2) | 1.000 |
| Heredity for inflammatory, rheumatic diseases, n (%) | 7 (23) | 33 (42) | 40 (36) | 0.078 |

Abbreviations:
PM, polymyositis;
DM, dermatomyositis;
IBM, inclusion body myositis;
JDM, juvenile dermatomyositis;
IQR, interquartile range;
MMT8, manual muscle test-8;
HAQ, health assessment questionnaire

TABLE 2

Clinical and muscle biopsy features

| Variable | aFHL1+ (n = 33) | aFHL1- (n = 99) | Sensitivity (%) | Specificity (%) | Positive predictive value (%) | Negative predictive value (%) | P value |
|---|---|---|---|---|---|---|---|
| Clinical muscle features, n (%) | | | | | | | |
| Muscle weakness | 33 (100) | 96 (98) | 25.58 | 100.00 | 100.00 | 2.04 | 1.000 |
| Proximal muscle weakness | 31 (100) | 93 (97) | 25.00 | 100.00 | 100.00 | 3.13 | 1.000 |
| Distal muscle weakness | 29 (94) | 68 (74) | 29.90 | 92.31 | 93.55 | 26.09 | 0.022 |
| Clinical atrophy | 21 (66) | 34 (37) | 38.18 | 83.82 | 65.63 | 62.64 | 0.007 |
| Myopathic EMG | 26 (87) | 73 (83) | 26.26 | 78.95 | 86.67 | 17.05 | 0.778 |

TABLE 2-continued

Clinical and muscle biopsy features

| Variable | aFHL1+ (n = 33) | aFHL1− (n = 99) | Sensitivity (%) | Specificity (%) | Positive predictive value (%) | Negative predictive value (%) | P value |
|---|---|---|---|---|---|---|---|
| Skin manifestations, n (%) | | | | | | | |
| Gottron's papules | 11 (33) | 31 (31) | 26.19 | 75.56 | 33.33 | 68.69 | 0.832 |
| Heliotrope rash | 8 (24) | 30 (30) | 21.05 | 73.40 | 24.24 | 69.70 | 0.658 |
| Mechanic's hands | 7 (22) | 15 (16) | 31.82 | 75.25 | 21.88 | 83.52 | 0.592 |
| Raynaud's phenomenon | 14 (44) | 35 (37) | 28.57 | 76.92 | 43.75 | 63.16 | 0.532 |
| Calcinosis | 4 (12) | 11 (11) | 26.67 | 75.00 | 12.12 | 88.78 | 1.000 |
| Shawl sign | 4 (13) | 13 (14) | 23.53 | 74.31 | 12.50 | 86.17 | 1.000 |
| Skin ulceration | 4 (12) | 3 (3) | 57.14 | 76.61 | 12.12 | 96.94 | 0.067 |
| V-sign | 7 (21) | 14 (14) | 33.33 | 76.15 | 21.21 | 85.57 | 0.413 |
| Extramuscular involvement, n (%) | | | | | | | |
| Interstitial lung disease | 9 (27) | 35 (35) | 20.45 | 72.73 | 27.27 | 64.65 | 0.523 |
| Dysphagia | 28 (85) | 52 (54) | 35.00 | 89.80 | 84.85 | 45.83 | 0.002 |
| Heart effect | 11 (33) | 37 (37) | 22.92 | 73.81 | 33.33 | 62.63 | 0.835 |
| Arrhythmia | 6 (18) | 22 (22) | 21.43 | 74.04 | 18.18 | 77.78 | 0.806 |
| Heart failure | 3 (9) | 14 (14) | 17.65 | 74.34 | 9.38 | 85.71 | 0.562 |
| Myocarditis/cardiomyopathy | 1 (3) | 4 (4) | 20.00 | 75.63 | 3.33 | 95.74 | 1.000 |
| Thrombosis/embolism | 5 (15) | 8 (9) | 38.46 | 75.00 | 15.15 | 91.30 | 0.326 |
| Vasculitis | 6 (18) | 3 (3) | 66.67 | 77.69 | 18.18 | 96.91 | 0.008 |
| Arthritis/synovitis | 15 (45) | 45 (45) | 25.00 | 75.00 | 45.45 | 54.55 | 1.000 |
| Muscle biopsy features, n (%) | | | | | | | |
| Inflammation | 30 (94) | 75 (81) | 28.57 | 90.00 | 93.75 | 19.35 | 0.098 |
| Endomysial inflammation | 19 (59) | 46 (52) | 29.23 | 76.79 | 59.38 | 48.31 | 0.537 |
| Perivascular inflammation | 22 (69) | 56 (63) | 28.21 | 76.74 | 68.75 | 37.08 | 0.668 |
| MHC class I expression in sarcolemma | 16 (80) | 47 (81) | 25.40 | 73.33 | 80.00 | 18.97 | 1.000 |
| Fiber necrosis | 7 (26) | 7 (9) | 50.00 | 78.49 | 25.93 | 91.25 | 0.042 |
| Perifascicular atrophy | 9 (28) | 18 (20) | 33.33 | 76.23 | 28.13 | 80.43 | 0.327 |
| Rimmed vacuoles | 5 (16) | 17 (18) | 22.73 | 73.53 | 15.63 | 81.52 | 0.795 |
| Invasion of non-necrotic fibers | 16 (52) | 28 (33) | 36.36 | 79.45 | 51.61 | 67.44 | 0.083 |
| Fiber degeneration/regeneration | 24 (80) | 52 (62) | 31.58 | 84.21 | 80.00 | 38.10 | 0.077 |
| Connective tissues/fat | 12 (44) | 11 (14) | 52.17 | 81.93 | 44.44 | 86.08 | 0.002 |
| Mitochondrial changes | 7 (32) | 7 (16) | 50.00 | 70.59 | 31.82 | 83.72 | 0.204 |

Abbreviations:
EMG, electromyogram;
MHC, major histocompatibility complex

TABLE 3

Clinical and laboratory measures

| Variable, median (IQR) | aFHL1+ (n = 33) | FHL1− (n = 99) | AUC | P value |
|---|---|---|---|---|
| MMT8 at latest visit | 74.5 (64.5-79.5) | 75 (63-79) | 0.521 | 0.743 |
| HAQ at latest visit | 0.88 (0.44-1.815) | 1.25 (0.5-1.75) | 0.474 | 0.686 |
| Highest measured serum ALAT | 1.24 (0.9-2.48) | 1.31 (0.88-2.52) | 0.485 | 0.801 |
| Highest measured serum ASAT | 1.08 (0.88-2.57) | 1.44 (0.79-2.65) | 0.494 | 0.911 |
| Highest measured serum CK | 12.9 (5.9-50) | 17.9 (8.1-52.8) | 0.467 | 0.569 |
| Highest measured serum LD | 12.5 (8.65-22.2) | 10.95 (7.6-18) | 0.559 | 0.319 |
| CRP at diagnosis, before treatment | 7 (5.5-12) | 10 (7-38) | 0.368 | 0.073 |

TABLE 3-continued

Clinical and laboratory measures

| Variable,<br>median (IQR) | aFHL1+<br>(n = 33) | FHL1−<br>(n = 99) | AUC | P value |
|---|---|---|---|---|
| SR at diagnosis, before treatment | 17 (10-35) | 22 (13-45.5) | 0.428 | 0.243 |

Abbreviations:
IQR, interquartile range;
AUC, area under the receiver operating characteristic curve;
MMT8, manual muscle test-8;
ALAT, alanine aminotransferase;
ASAT, aspartate aminotransferase;
CK, creatine kinase;
LD, lactate dehydrogenase;
CRP, C-reactive protein;
SR, sedimentation rate

TABLE 4

Autoantibody data

| Autoantibody, n (%) | aFHL1+<br>(n = 33) | aFHL1−<br>(n = 99) | P value |
|---|---|---|---|
| ANA | 23 (77) | 43 (61) | 0.1202 |
| Jo-1 | 3 (9) | 20 (20) | 0.1888 |
| SRP | 2 (6) | 3 (3) | 0.6029 |
| Ro52 | 14 (42) | 31 (32) | 0.2589 |
| U1RNP | 6 (18) | 7 (7) | 0.0636 |

Abbreviations:
ANA, antinuclear antibodies

To further strengthen this observation, a scoring system to investigate the clinical outcome of patients of the Swedish cohort with a specific focus on muscle involvement at the last medical examination available was developed. Within this scoring system also the overall damage as identified using the International Myositis Assessment & Clinical Studies Group (IMACS) myositis damage index (MDI) VAS score (Isenberg et al. *International consensus outcome measures for patients with idiopathic inflammatory myopathies. Development and initial validation of myositis activity and damage indices in patients with adult onset disease*. Rheumatology (Oxford) 2004, 43(1):49-54) was considered. It was found that patients with anti-FHL1 autoantibodies had a significantly worse outcome score compared to patients without this autoantibody (FIG. 4C). Most importantly, patients with the highest disease score were found in the anti-FHL1+ group. These patients, who can be characterized by a high degree of muscle weakness or complete loss of ambulation, had a remarkably progressive and therapy-resistant history of disease. Furthermore, histological characteristics of anti-FHL1+ and anti-FHL1− patients were compared by scoring of coded sections stained with hematoxylinkosin and Gomori trichrome of anti-FHL1+ patients with gender, age- and diagnosis (PM, DM and IBM)- matched anti-FHL1 negative patients according to a visual analog scale (VAS). A more overall severe histopathology was observed in patients having anti-FHL1 compared to patients without anti-FHL1 autoantibodies (FIG. 4D), which is consistent with the already observed association between anti-FHL1 positivity and distinct muscle biopsy features (FIG. 4A). Anti-FHL1+ patients had a mean VAS score of 2.8 cm whereas anti-FHL1− patients only had a score of 0.9 cm (FIG. 4D). In particular, anti-FHL1+ patients had more connective tissue/fat replacement, higher amounts of internal nuclei, massive variation of fiber size and more often tremendous inflammatory infiltrates. In agreement with the scoring for the disease severity, also the histopathological examination revealed that patients with the highest possible score between 6.0 and over 8.0 cm on the VAS were found in the anti-FHL1+ group as in these patients a severe muscle histopathology was observed.

FHL1 Shows a Different Expression Pattern and Localization in Muscles of Myositis Patients Compared to Healthy Muscle Tissue.

To gain insights into mechanisms of muscle damage related to anti-FHL1+ inflammatory myopathies, the expression of the protein in muscle tissue of myositis patients positive for anti-FHL1 autoantibodies compared to muscle tissue from healthy individuals was examined by immunofluorescence staining and confocal microscopy. Healthy muscle tissue and muscle of anti-FHL1-patients displayed a homogenous expression pattern of FHL1 that is mainly intracellular and distributed uniformly along the muscle fiber. A remarkably different expression pattern was detected when examining myositis patients with anti-FHL1 autoantibodies. Here, some fibers had a very high FHL1 expression with some focal accumulations whereas other fibers seemed to nearly completely have lost the expression of FHL1. In addition, co-localization of FHL1 with laminin was observed in the sarcolemma of myositis patients that was less obvious in healthy control muscle tissue. Specificity of the staining was confirmed by using appropriate isotype controls and by blocking FHL1 staining with recombinant FHL1.

Next, FHL1 protein expression in muscle lysates of myositis patients and healthy controls was examined by western blot. As shown in FIG. 5A, in healthy control muscle samples one major band was detectable at around 38 kDa. Additionally to this 38 kDa band, in muscle lysates of patients, especially in those having anti-FHL1 autoantibodies, a strong expression of two further bands, at 34 kDa and at 25 kDa was detected (FIG. 5A). When quantifying the intensity of those 3 bands and normalizing them to expression of the housekeeping gene GAPDH, it became obvious that expression of the 38 kDa band was comparable between muscles of healthy controls and myositis patients with a tendency of a lower expression in anti-FHL1+ vs anti-FHL1− patients (FIG. 5B). By contrast, expression intensity of the 34 and 25 kDa band consistently increases from healthy control muscle to anti-FHL1− tissue and reaches a maximum in muscle lysates from anti-FHL1+ patients (FIG. 5B). FHL1 is undergoing alternative splicing and different protein isoforms are described (Shathasivam ibid). To check if the differences in protein expression detected by western blot are due to expression of different isoforms on mRNA level, mRNA expression analysis for the 3 major FHL1 isoforms (isoform A, B and C) was performed. All three isoforms were expressed similarly in healthy control, anti-FHL1⁻ and anti-FHL1⁺ muscle tissue (FIG. 5C) with a tendency of a lower expression of isoform A in anti-FHL1⁺ vs anti FHL1⁻ patients. In summary, muscle tissues from anti-FHL1⁺ patients showed a distinct protein expression pattern as shown by both, confocal and western blot analysis. Possibly the bands represent cleavage fragments caused by degradation or proteolytic cleavage of FHL1 autoantigen in the diseased muscle.

FHL1 is Susceptible to Cleavage by Granzyme B.

Many autoantigens in autoimmune diseases including myositis and scleroderma are substrates of serine/cysteine proteases such as granzyme B or caspases (Rosen et al. *Autoantigens as substrates for apoptotic proteases: implications for the pathogenesis of systemic autoimmune disease*. Cell Death Differ 1999, 6(1):6-12). Since this could reveal the exposure of neo-epitopes and thus explain the presence of autoantibodies against FHL1, we addressed the question if FHL1 might be cleaved by proteases performing cleavage assays with lysates from human skeletal muscle cells. Indeed, FHL1 was identified to be a target of proteases in muscle cells as a dose-dependent fragmentation of FHL1 with increasing concentration of granzyme B could be observed (FIG. 6A). Presence of different caspase inhibitors such as z-Vad and z-DEVD could not prevent cleavage of FHL1 (FIG. 6B). Consequently, FHL1 is a direct substrate of granzyme B with a resulting cleavage fragment of 30 kDa. Cleavage of FHL1 by granzyme B was also observed by using recombinant proteins; all available recombinant proteins including a His-tagged FHL1 protein (FIG. 6C), a commercially available FHL1 protein (FIG. 6D) and the FHL1-MaBP fusion protein (FIG. 2E) were cleaved and the 30 kDa cleavage fragment could be detected. As this fragment under conditions used in FIG. 6E was detectable both with an antibody binding to the N-terminus and another antibody binding to the C-terminus of the protein, the cleavage site is located on the N-terminal part of the protein (FIG. 6E, scheme). According to tetrapeptide specificity and the fragment sizes generated by granzyme B cleavage, this cleavage site was identified to have the sequence IGAD with P1 aspartic acid at amino acid position 50 (FIG. 6F). The identified cleavage site was confirmed be site directed mutagenesis of D50->A50 leading to insusceptibility of FHL1 protein to be cleaved by granzyme B whereas in contrast wildtype FHL1 was cleaved as expected (FIG. 6G).

To further investigate if granzyme B cleavage of FHL1 increases immunoreactivity to this protein, recombinant FHL1 was cleaved and serum reactivity of anti-FHL1⁺ and anti-FHL1⁻ patients as well as healthy controls was analyzed by ELISA and compared to reactivity to unleaved protein. Immunoreactivity was increased if FHL1 is cleaved by granzyme B compared to uncleaved protein as evident by using both, His-tag-FHL1 (FIG. 7A) and MaBP-FHL1 (FIG. 7B). A striking and statistically significant increase in reactivity was especially detected when sera from anti-FHL1⁺ patients were used. Here, for 12 of 15 sera more than a two-fold increase in absorbance could be detected. To a lower extent, this increase could be also observed for sera of anti-FHL1⁻ patients and healthy controls (FIG. 7A, B). To confirm a higher immunoreactivity towards cleaved FHL1, recombinant FHL1-MaBP was cleaved by granzyme B and immunoprecipitated with sera from different anti-FHL1⁺ or anti-FHL1⁻ patients as well as healthy controls. As expected, the signal was much higher if sera from anti-FHL1⁺ patients were used for immunoprecipitation compared to anti-FHL1⁻ or healthy control sera (FIG. 7C). If FHL1-MaBP was cleaved by granzyme B, the autoantibodies in anti-FHL1⁺ serum not only recognize the full length form of the fusion protein, but also the 30 kDa cleavage fragment. Quantification of the signals and summation of the intensities for the two bands confirmed a higher serum immunoreactivity if the protein is cleaved by granzyme B (FIG. 7D).

3. Conclusions

Myopathies are skeletal muscle disorders, with genetic or autoimmune mediated origin, which are characterized by progressive weakness, degeneration and atrophy of the muscle. Importantly, studies of genetically based muscular dystrophies provide emerging evidence that FHL1 is the causative gene for several X-linked myopathies. The present inventors have used a molecular cloning strategy, and identified FHL1 as a novel antigenic target in IIM and thus extended current knowledge about FHL1 and its role in muscle-specific pathology. Autoantibodies to FHL1 in patients with IIM were detected at proportionate high frequencies of 25% in different cohorts whereas patients suffering from other autoimmune diseases or other hereditary myopathies did not display autoantibody reactivity towards FHL1. A clear difference in the expression pattern of FHL1 in antibody positive patients with an inflammatory myopathy versus healthy muscle tissue as evident by confocal microscopy was also found. This characteristic expression pattern is not only very similar to that observed in muscular disorders caused by mutations of FHL1 (Schessl ibid), indicating that the protein in skeletal muscle fibers might be affected by pathogenic modifications possibly inducing the production of autoantibodies. One of such disease mechanism could be the susceptibility of FHL1 to cleavage by the serine protease granzyme B as the cleavage products could probably initiate an autoimmune response towards this protein. The identified autoantibodies are significantly associated with progressive muscle weakness, muscle atrophy, dysphagia as well as a poor clinical outcome as evident by clinical and muscle biopsy features. Thus, anti-FHL1 autoantibodies represent novel and highly attractive biomarkers for IIM characterized by a severe involvement of skeletal muscle and a risk of poor prognosis.

Already known and well-described autoantibodies in inflammatory myopathies can be found in more than half of the patients with this disease and they are useful in predicting clinical outcome, response to therapy, and in immunogenetics (Hengstman et al. *Myositis-specific autoantibodies: overview and recent developments*. Curr Opin Rheumatol 2001, 13(6):476-482; Targoff ibid). Although these autoantibodies are myositis-specific, meaning they are characteristic for IIM and are not detected in other chronic inflammatory diseases, they do not completely explain the disease manifestations, as the targeted antigens are not specific for muscle tissue. Instead, the myositis-specific antibodies target a ubiquitously active group of intracellular molecules of the transcriptional machinery, including tRNA synthetases (e.g. Jo1) and signal recognition particles (SRP), or components of the nucleosome remodelling complex, such as Mi-2. It is not known whether these autoantibodies play a role in IIM pathology. Therefore, the triggers for the observed immune response and the main targets of autoimmunity in IIM remain to be discovered. A few muscle-specific autoantigens in human inflammatory myopathies (Salajegheh ibid; Larman ibid) or animal forms of IIM (Wu et al. *Autoantibodies in canine masticatory muscle myositis recognize a novel myosin binding protein-C family member*.

J Immunol 2007, 179(7):4939-4944; Evans et al. *Canine inflammatory myopathies: a clinicopathologic review of 200 cases*. J Vet Intern Med 2004, 18(5):679-691; Hankel et al. *Sarcolemma-specific autoantibodies in canine inflammatory myopathy*. Vet Immunol Immunopathol 2006, 113(1-2):1-10) have recently been identified. The present inventors have identified FHL1, a protein with a previously described role in monogenetic muscular dystrophies, as a major target for muscle-specific autoantibodies in human IIM. This autoantibody was only detected in IIM, but not in other chronic inflammatory diseases qualifying it as a myositis-specific autoantibody (FIG. 3). Importantly, anti-FHL1 autoantibodies could not be identified in genetically based neuromuscular diseases (FIG. 3). Thus, it is unlikely that autoantibodies against FHL1 are just an epiphenomenon of myofiber damage and associated exposure of sequestered proteins to the immune system.

Figure 5:
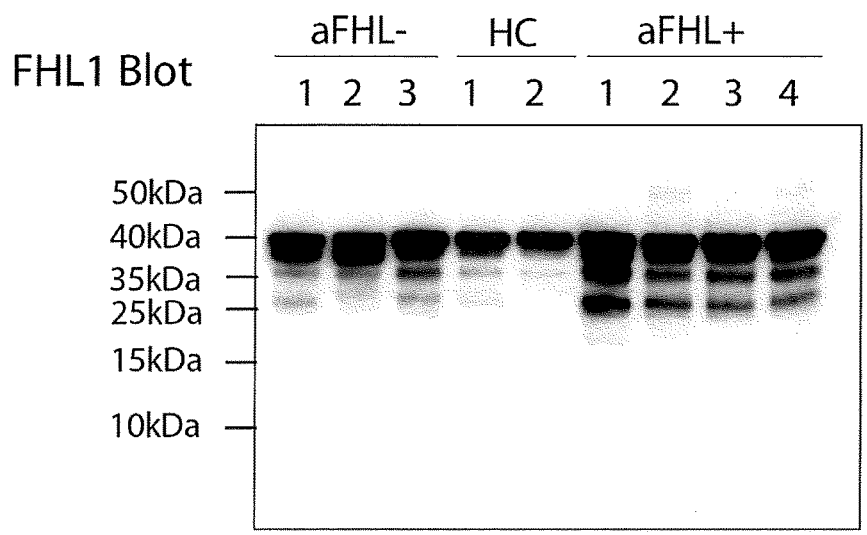
Figure 5:
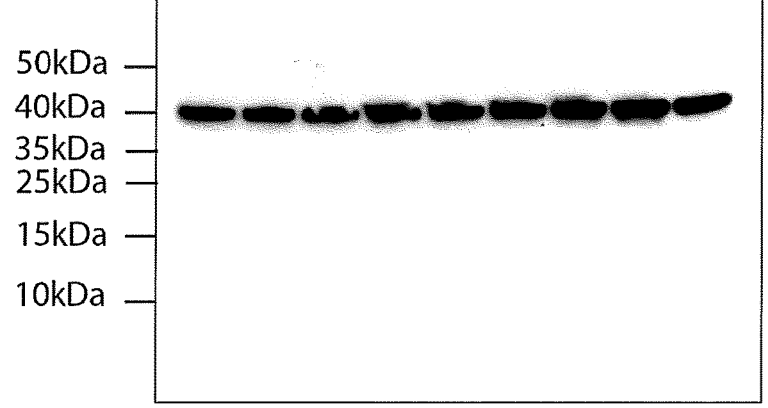
Figure 5:
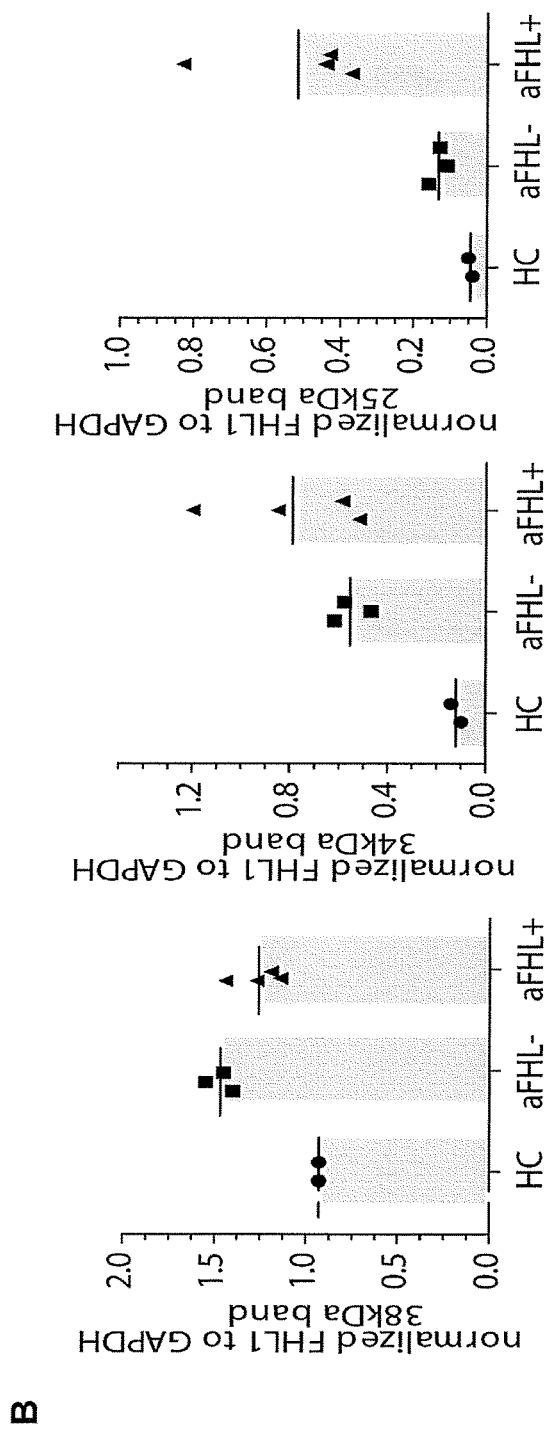
Figure 5:
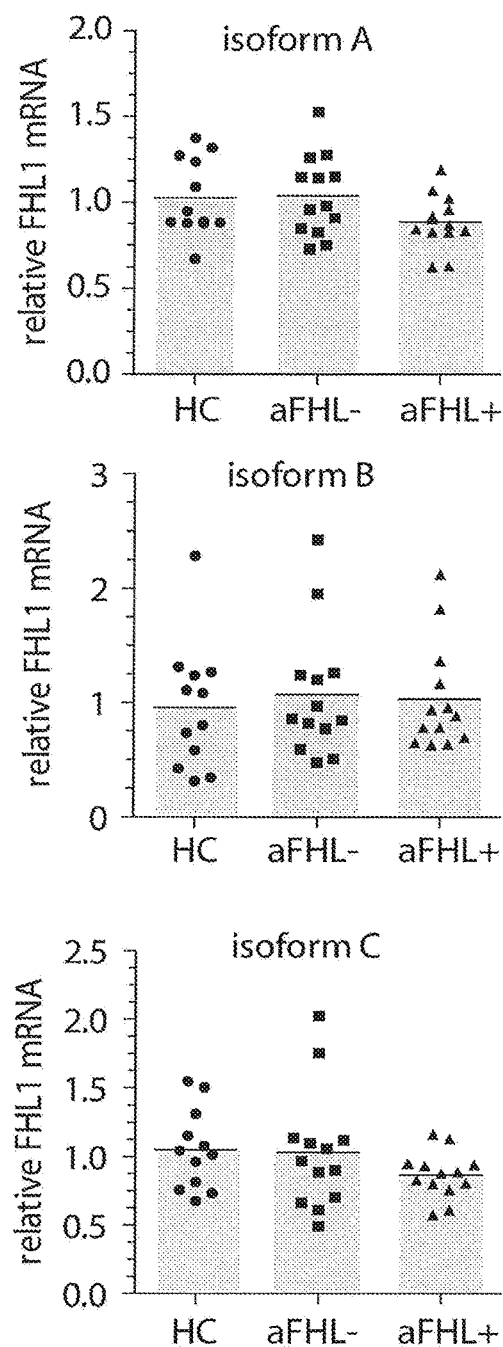

Myofiber damage and often severely abnormal muscle histology in many patients with anti-FHL1 autoantibodies became obvious by histopathological examinations (FIG. 4D). The correlation between presence of autoantibodies to FHL1 and a severe histopathology as well as a high clinical score in particular affecting performance of the muscles and dysphagia as well as other muscle affecting clinical variables (FIG. 4A-C) was highly statistically significant. Dysphagia has been described to be associated with a high disease severity in IIM (Horowitz ibid; Carpenter et al. *Survival in polymyositis: corticosteroids and risk factors*. J Rheumatol 1977, 4(2):207-214. One possible explanation for these correlations is that formation of the autoantibodies is a clear sign of pathogenic changes of FHL1 protein in the skeletal muscle that occur in a subset of patients with features of an inflammatory myopathy. Regarding pathogenic changes of FHL1 protein in IIM, evidence is provided by confocal microscopy of affected muscle tissue compared to healthy muscle, that muscles from patients with anti-FHL1 antibodies displayed clear changes in the expression pattern of FHL1 protein. In healthy muscle, FHL1 is expressed homogenously over the whole muscle fiber and expression is primarily intracellular. By contrast, for anti-FHL1+ muscle, a co-localization of FHL1 with laminin, was observed using confocal microscopy suggesting that FHL1 is expressed at or close to the sarcolemma in addition to an intracellular expression. A location in the sarcolemma would expose it directly to the immune system and be a trigger for an autoimmune reaction. Moreover, it could make the muscle fiber directly accessible to potential pathogenic autoantibodies. In SLE for example, there is a close association between presence of autoantibodies against DNA and chromatin and an abnormal activation of the complement system. Interestingly, it was found that patients with anti-FHL1 autoantibodies compared to anti-FHL negative patients more frequently had the HLA DRB1*03/13 genotype (FIG. 4B). Individuals with this particular genotype have substantial polymorphisms in the region occupied by the C4 complement genes, which could, together with the formation of potential pathogenic autoantibodies, contribute to initiation and maintenance of the disease. In addition to a co-localization with the sarcolemma, in muscle tissue of patients with anti-FHL1 autoantibodies, FHL1 shows focal accumulations: some fibers show a tremendously high activity of the protein, and others seem to completely loose FHL1 expression. This specific expression pattern is similar to that observed by immunofluorescence in patients suffering from RBM (Schessl ibid). RBM is caused by mutations of FHL1 affecting the highly conserved zinc-coordinating histidine and cysteine residues of FHL1 consequently leading to instability of the secondary structure, misfolding and aggregation of the protein. The protein appears to be progressively incorporated into intracytoplasmic inclusions and elevated total FHL1 content can be detected in the biopsies. The latter is in agreement with our data from western blot analysis of biopsy material from myositis with higher FHL1 contents compared to healthy muscle tissue (FIG. 5). Interestingly, enhanced expression of autoantigens in myositis versus healthy muscle tissue appears to be a commonly observed phenomenon in IIM (Casciola-Rosen et al. *Enhanced autoantigen expression in regenerating muscle cells in idiopathic inflammatory myopathy*. J Exp Med 2005, 201(4): 591-601). In case of FHL1, it seems that the amount of lower molecular size forms (bands migrating at 34 and 25 kDa) increases in diseased muscle tissue compared to the commonly expressed isoform A migrating at 38 kDa. For the latter no differences were observed between healthy and IIM muscle. On mRNA level the three major FHL1 isoforms are expressed equally with a tendency of an even lowered expression of isoform A in anti-FHL1+ muscle (FIG. 5). The different expression pattern of FHL1 detected by Western Blot is thus either due to posttranslational modification or fragmentation of the protein.

Multiple studies have demonstrated that the majority of autoantigens targeted in systemic autoimmune diseases are substrates for granzymes, in particular for granzyme B (Casciola-Rosen et al. *Cleavage by granzyme B is strongly predictive of autoantigen status: implications for initiation of autoimmunity*. J Exp Med 1999, 190(6):815-826), a serine protease found in the cytoplasmic granules of cytotoxic CD8+ T lymphocytes and natural killer cells. Interestingly, in polymyositis, T cells in close contact with muscle fibers have been shown to direct their cytolytic granule components towards the site of cell-cell contact (Goebels et al. *Differential expression of perforin in muscle-infiltrating T cells in polymyositis and dermatomyositis*. J Clin Invest 1996, 97(12):2905-2910. Moreover, clonal expansion of autoantigenic T cells in the inflamed target tissue can be observed as indicative by a restricted T cell receptor repertoire of CD8+ T cells invading muscle fibers in polymyositis (Bender et al. *T cell receptor repertoire in polymyositis: clonal expansion of autoaggressive CD8+ T cells*. J Exp Med 1995, 181(5):1863-1868). Granzyme B cleavage of autoantigens can lead to generation of neoepitopes and thus promote initiation of an immune response (Darrah et al. *Granzyme B cleavage of autoantigens in autoimmunity*. Cell Death Differ 2010, 17(4):624-632), but it can also influence protein function as well as redistribution within the cell. It could be demonstrate here, that FHL1 is a substrate of granzyme B (FIG. 6). The cleavage site could be detected to be IGAD at amino acid position 50. Moreover evidence that cleavage of FHL1 causes a higher immunoreactivity towards this protein is provided (FIG. 7). Susceptibility to granzyme B cleavage thus could drive exposure of novel FHL1 epitopes and lead to a subsequent break of tolerance and initiation of autoimmunity. Moreover, it could also induce instability of the secondary structure of FHL1 protein similar to that observed in FHL1-related genetic muscular dystrophies which consequently might result in loss of protein functionality.

In conclusion, the present inventors have identified and characterized a novel myositis- and muscle-specific autoantigen target in patients classified as having IIM with severe skeletal muscle involvement and poor prognosis. Autoantibodies specific to FHL1 represent biomarkers for prognostic value in this disease. Further investigations on FHL1 and its corresponding autoantibodies in IIM may shed some light on possible mechanisms of the development of autoimmunity in inflammatory muscle disease.

The invention claimed is:

1. A method for diagnosis of an idiopathic inflammatory myopathy, said method comprising:

detecting autoantibodies specific for FHL 1 in a blood sample obtained from a human subject; and diagnosing the idiopathic inflammatory myopathy in the human subject based on detection of the autoantibodies specific for FHL 1, wherein the antibodies specific for FHL 1 are detected using an immunoassay detecting reactivity to a recombinant FHL 1-MaBP fusion protein or a recombinant His-tag FHL 1 fusion protein.

2. A method for assessing a subject's risk of developing an idiopathic inflammatory myopathy, said method comprising:

detecting autoantibodies specific for FHL 1 in a blood sample obtained from a human subject; and assessing the subject's risk of developing the idiopathic inflammatory myopathy based on detection of the autoantibodies specific for FHL 1, wherein the antibodies specific for FHL 1 are detected using an immunoassay detecting reactivity to a recombinant FHL 1-MaBP fusion protein or a recombinant His-tag FHL 1 fusion protein.

3. A method for assessing the severity and/or prognosis of an idiopathic inflammatory myopathy, said method comprising:
- detecting autoantibodies specific for FHL 1 in a blood sample obtained from a human subject; and
- assessing the severity and/or the prognosis of the idiopathic inflammatory myopathy based on detection of the autoantibodies specific for FHL 1, wherein the antibodies specific for FHL 1 are detected using an immunoassay detecting reactivity to a recombinant FHL 1-MaBP fusion protein or a recombinant His-tag FHL 1 fusion protein.

4. The method according to claim 1, wherein the antibodies specific for FHL1 are detected by ELISA, RIA, or radioimmunoprecipitation assays, by surface plasmon resonance, or by electrochemiluminescence.

5. The method according to claim 1, wherein the blood sample is serum or plasma.

6. The method according to claim 2, wherein the blood sample is serum or plasma.

7. The method according to claim 3, wherein the blood sample is serum or plasma.

8. The method according to claim 2, wherein the antibodies specific for FHL1 are detected by ELISA, RIA, or radioimmunoprecipitation assays, by surface plasmon resonance, or by electrochemiluminescence.

9. The method according to claim 3, wherein the antibodies specific for FHL1 are detected by ELISA, RIA, or radioimmunoprecipitation assays, by surface plasmon resonance, or by electrochemiluminescence.

* * * * *

SEQUENCE LISTING

```
<160> NUMBER OF SEQ ID NOS: 5

<210> SEQ ID NO 1
<211> LENGTH: 32
<212> TYPE: DNA
<213> ORGANISM: Artificial sequence
<220> FEATURE:
<223> OTHER INFORMATION: Primer

<400> SEQUENCE: 1
caacaagaat tcatggcgga gaagtttgac tg                                     32

<210> SEQ ID NO 2
<211> LENGTH: 31
<212> TYPE: DNA
<213> ORGANISM: Artificial sequence
<220> FEATURE:
<223> OTHER INFORMATION: Primer

<400> SEQUENCE: 2
caacaagtcg acttacagct ttttggcaca g                                      31

<210> SEQ ID NO 3
<211> LENGTH: 25
<212> TYPE: DNA
<213> ORGANISM: Artificial sequnce
<220> FEATURE:
<223> OTHER INFORMATION: Probe

<400> SEQUENCE: 3
ctcctcgagg cccgggtttg gtaaa                                             25

<210> SEQ ID NO 4
<211> LENGTH: 21
<212> TYPE: DNA
<213> ORGANISM: Artificial sequence
<220> FEATURE:
<223> OTHER INFORMATION: Probe

<400> SEQUENCE: 4
accccatcac tgggtttggt a                                                 21

<210> SEQ ID NO 5
<211> LENGTH: 18
<212> TYPE: DNA
<213> ORGANISM: Artificial sequence
<220> FEATURE:
<223> OTHER INFORMATION: Probe

<400> SEQUENCE: 5
agtgcaacaa gggtttgg                                                     18
```